United States Patent
Murphy et al.

(10) Patent No.: US 12,421,281 B2
(45) Date of Patent: Sep. 23, 2025

(54) CYCLOSPORINE COMPOSITIONS AND METHODS OF USE

(71) Applicant: Bacainn Biotherapeutics, Ltd., George Town (KY)

(72) Inventors: Chris Murphy, Upton, MA (US); Ronald Farquhar, Boston, MA (US); Roland E. Dolle, Eureka, MO (US)

(73) Assignee: Bacainn Biotherapeutics, Ltd., George Town (KY)

( * ) Notice: Subject to any disclaimer, the term of this patent is extended or adjusted under 35 U.S.C. 154(b) by 613 days.

(21) Appl. No.: 17/891,351

(22) Filed: Aug. 19, 2022

(65) Prior Publication Data

US 2023/0192771 A1   Jun. 22, 2023

Related U.S. Application Data

(63) Continuation of application No. PCT/US2021/018999, filed on Feb. 22, 2021.

(60) Provisional application No. 62/981,750, filed on Feb. 26, 2020.

(51) Int. Cl.
*A61P 17/00* (2006.01)
*A61P 29/00* (2006.01)
*C07K 7/64* (2006.01)

(52) U.S. Cl.
CPC .............. *C07K 7/645* (2013.01); *A61P 17/00* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 9,453,051 B2 * | 9/2016 | Fischer | A61P 13/12 |
| 10,065,992 B2 * | 9/2018 | Frydrych | A61P 37/08 |
| 2009/0170218 A1 * | 7/2009 | Zheng | C07K 7/645 |
| | | | 436/501 |
| 2012/0196749 A1 | 8/2012 | Fischer et al. | |

OTHER PUBLICATIONS

Lichtiger et al (Gastroenterolgy and Hepatology 2:624-626, 2006) (Year: 2006).*
Sandborn et al (Mayo Clin Proc 67:981-990, 1992) (Year: 1992).*
Rajagopalan et al (Indian Dermatology Online Journal 13:585-599, 2022) (Year: 2022).*
Kacmaz et al (Ophthalmology 117:576-584, 2010) (Year: 2010).*
International Search Report & Written Opinion on PCT Application No. PCT/US2021/018999 dated May 19, 2021.

* cited by examiner

*Primary Examiner* — Craig D Ricci
(74) *Attorney, Agent, or Firm* — Foley & Lardner LLP

(57) ABSTRACT

Disclosed herein are cyclosporine compounds and methods for use in the treatment or prevention of neutrophil-mediated inflammation, wherein the compounds inhibit the activity of MRP2 and FPRL.

18 Claims, 5 Drawing Sheets

CYCLOSPORINE COMPOSITIONS AND METHODS OF USE

CROSS-REFERENCE TO RELATED APPLICATION

This application claims the benefit of and priority to U.S. Provisional Application No. 62/981,750 filed on Feb. 26, 2020, the entire disclosure of which is incorporated herein by reference in its entirety.

TECHNICAL FIELD

The technology of the present disclosure relates to methods, compounds, and compositions for treating or preventing disease associated with neutrophil-mediated inflammation.

BACKGROUND

Inflammation, and in particular chronic inflammatory disease (CID), is globally highly prevalent and is viewed as one of the major causes for the development of different diseases like cancer, cardiovascular disease, diabetes, obesity, osteoporosis, rheumatoid arthritis, inflammatory bowel disease, asthma, and CNS related diseases such as depression and Parkinson's disease. Epithelial cells dramatically increase surface expression of the membrane ABC transporter multidrug resistance protein 2 (MRP2) in response to infection with *Salmonella enterica* serovar Typhimurium (*Salmonella* typhimurium) or a variety of other pathogens. The intracellular biosynthetic pathway of the eicosanoid $HXA_3$ is concurrently upregulated, and increased MRP2 at the surface serves to transport $HXA_3$ into the intestinal lumen. This establishes a concentration gradient of $HXA_3$ across the epithelium that directs chemotaxis of neutrophils from the basolateral side into the lumen, resulting in a critical inflammatory process. Hence, inhibition of MRP2 is an avenue for the treatment or prevention of inflammatory disease.

Gluten-containing cereals, e.g., wheat, rye and barley, are an important part of the human diet. However, gliadin, the main component of gluten, has been implicated in a variety of disorders including celiac disease, irritable bowel syndrome, non-celiac gluten sensitivity, type 1 diabetes, schizophrenia, and autism. It has been shown that gliadin increases gut epithelial permeability, and acts as a neutrophil chemoattractant factor of similar potency to fMet-Leu-Phe through binding to FPR1. Hence, inhibition of FPR1 is an avenue for the treatment or prevention of gliadin-related conditions.

SUMMARY

In one aspect, the present disclosure relates to compounds of Formula I and pharmaceutical compositions thereof.

The compounds of Formula I have the following structure, and include stereoisomers thereof and pharmaceutically acceptable salts of the foregoing:

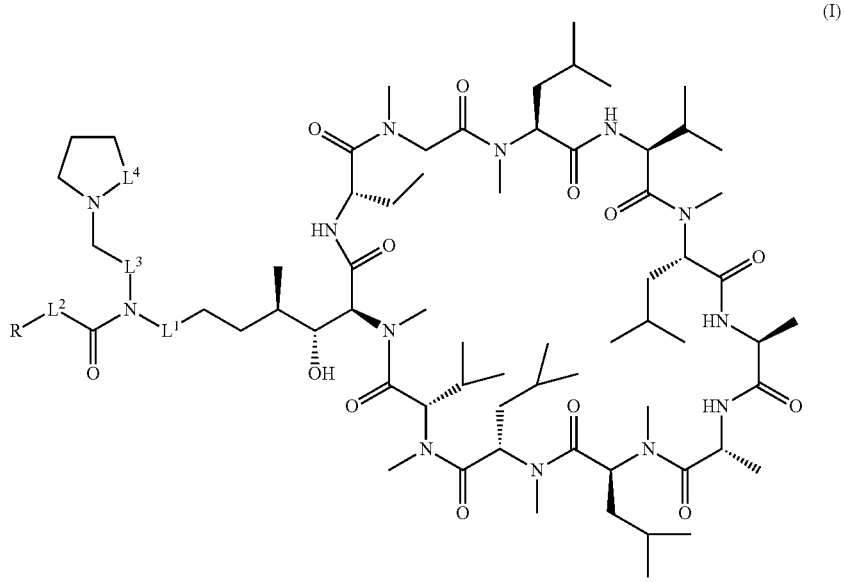

(I)

wherein
$L^1$ is a $C_{1-6}$ alkylene group;
$L^2$ is absent or is a linker selected from O, NH, or a $C_{1-12}$ alkylene or heteroalkylene group;
$L^3$ is a $C_{1-6}$ alkylene group;
$L^4$ is a methylene or ethylene group; and
R is a polyethylene glycol (PEG) group.

In some embodiments of compounds of Formula I, $L^1$ may be a $C_{1-6}$ alkylene group. For example, $L^1$ may be a propylene group.

In some embodiments of compounds of Formula I, $L^2$ may be absent. In some embodiments, $L^2$ may be a $C_{1-6}$ alkylene group, e.g., a methylene group.

In some embodiments of compounds of Formula I, $L^3$ may be a methylene group.

In some embodiments of compounds of Formula I, $L^4$ may be a methylene group.

In some embodiments of compounds of Formula I, R may be a PEG terminated with OH or a $C_{1-6}$ alkoxy group.

In some embodiments of compounds of Formula I, R may be a PEG terminated with OH or a $C_{1-6}$ alkoxy group. In some embodiments, R may be a PEG having a weight average molecular weight of from about 100 Da to about 20 kDa, including, e.g., about 1 kDa to about 5 kDa.

In some embodiments the compounds of Formula I, stereoisomers thereof, and pharmaceutically acceptable salts of the foregoing have the structure of Formula IA:

In some embodiments, the urogenital disease comprises a urinary tract infection.

In some embodiments, the sexually transmitted disease is selected from the group consisting of pelvic inflammatory disease, gonorrhea infection, *chlamydia* infection, herpes, and urethritis.

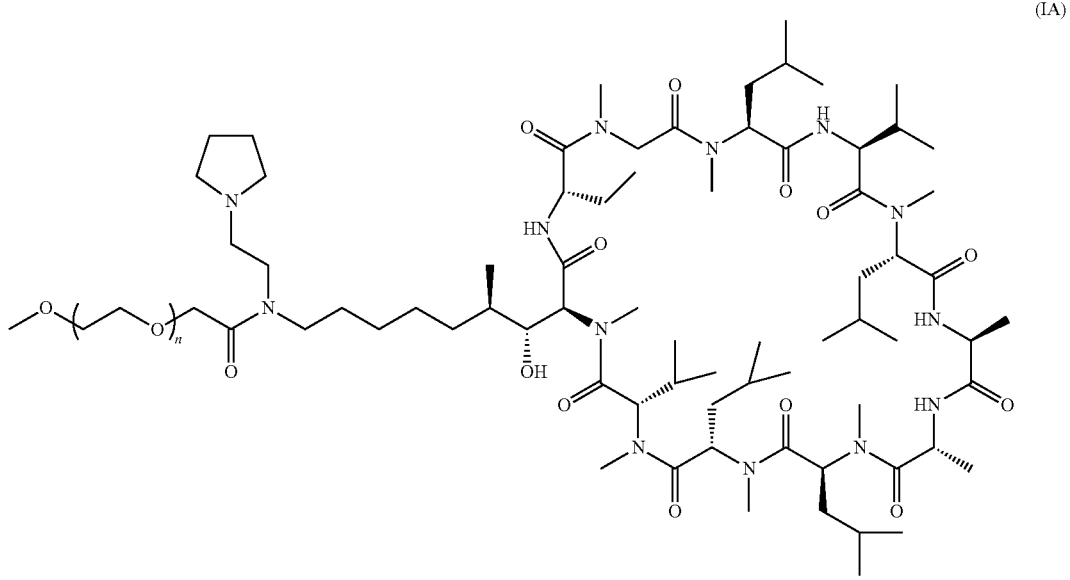

(IA)

wherein n is an integer from 40 to 50.

In another aspect, the present disclosure relates to a pharmaceutical composition including any of the compounds disclosed herein (including but not limited to compounds of Formula I and IA) and a pharmaceutically acceptable carrier.

In another aspect, the present disclosure relates to methods for treating a disease associated with neutrophil-mediated inflammation in a target tissue of a mammalian subject in need thereof, comprising administering to the subject a therapeutically effective amount of a compound of Formula I, including but not limited to any of the embodiments disclosed herein, such as a compound of Formula IA.

In some embodiments, the disease is selected from the group consisting of intestinal disease, colitis, inflammatory lung disease, inflammatory skin disease, ocular disease, urogenital disease, and sexually transmitted diseases.

In some embodiments, the intestinal disease is selected from the group consisting of proctitis, orchitis, Crohn's disease, and celiac disease.

In some embodiments, the colitis is selected from the group consisting of ulcerative colitis, also known as colitis ulcerosa, infectious/non-infectious enterocolitis, and inflammatory bowel disease (IBD).

In some embodiments, the inflammatory lung disease is selected from the group consisting of pneumococcal infection, asthma, chronic obstructive pulmonary disease (COPD), and pulmonary fibrosis.

In some embodiments, the inflammatory skin disease is selected from the group consisting of dermatitis (eczema), rosacea, seborrheic dermatitis, and psoriasis.

In some embodiments, the ocular disease is selected from the group consisting of uveitis, retinitis, keratitis, and macular degeneration.

In some embodiments, the administering step is selected from the group consisting of topical administration and administration at a luminal surface of the target tissue.

In some embodiments, the inflammation is non-infectious inflammation. In some embodiments, the inflammation is infectious inflammation.

In some embodiments, the method further comprises administering to the subject a therapeutically effective amount of one or more second compound that inhibits one or more of multidrug resistance protein 2 (MRP2) and $HXA_3$ synthase, wherein the therapeutic amount of the second compound reduces migration of neutrophils into the target tissue.

In some embodiments, the method further comprises administering to the subject a therapeutically effective amount of one or more compounds that increases multidrug resistance protein 1 (MRP1), wherein the therapeutic amount of the third compound reduces migration of neutrophils into the target tissue.

In some embodiments, the method further comprises administering one or more compounds that inhibits one or more of multidrug resistance protein 2 (MRP2) and hepoxilin A3 ($HXA_3$) synthase, wherein the therapeutic amount of the second compound reduces migration of neutrophils into the target tissue.

In some embodiments, the method further comprises administering to the subject a therapeutically effective amount of one or more compounds that increases one or more N-acylethanolamines (NAEs), wherein the therapeutic amount of the third compound reduces migration of neutrophils into the target tissue.

In some embodiments, the inflammation is associated with Crohn's disease and the treatment or prevention further comprises administering one or more mesalamine products, corticosteroid formulations, ileal-release budesonide, glucocorticosteroids/EEN immunomodulatives, including azathioprine, 6-mercaptopurine, and methotrexate, anti-tumor necrosis factor (TNF) drugs, including infliximab, adalimumab, and certolizumab, pegol, anti-alpha-4 beta-7 integrin antibody vedolizumab, ABT-494, and filgotinib.

In some embodiments, the inflammation is associated with ulcerative colitis and the treatment or prevention further comprises administering one or more of 5-aminosalicylates, mesalamine, corticosteroids, multimatrix budesonide, azathioprine, 6-mercaptopurine, anti-TNF drugs, including infliximab, adalimumab, and golimumab, vedolizumab, tofacitinib, ABT-494, and filgotinib.

In some embodiments, the method further comprises administering one or more antibiotic and/or anti-inflammatory agents selected from the group consisting of: Dalbavancin, Oritavancin, Cubicin, Tedizolid, Ceftobiprole, Ceftobiprole, Ceftolozane-tazobactam, mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, flurandrenolone, fluclorolone acetonide, fludrocortisone, flumethasone pivalate, fluosinolone acetonide, fluocinonide, fluocortin butylester, fluocortolone, fluprednidene (fluorenylidene)acetate, flurandrenolone, halcinonide, hydrocortisone acetate, hydrocortisone butyrate, methylprednisolone, triamcinolone acetonide, cortisone, cortodoxone, fluocinonide, fludrocortisone, diflorasone diacetate, flurandrenolone acetonide, medrysone, amciafel, amcinafide, betamethasone, chloroprednisone, chloroprednisone acetate, clocortolone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppressant agents such as cyclosporin, and cytokine synthesis inhibitors, tetracycline, minocycline, and doxycycline, or any combination thereof.

In some embodiments, the method further comprises administering one or more antibodies selected from the group consisting of: antibodies targeting *Clostridium difficile* toxins, antibodies targeting tumor necrosis factor (TNF), antibodies targeting interleukins, and antibodies targeting metalloproteinase-9.

In some embodiments, the compound of formula I reduces migration of neutrophils into the target tissue as compared to untreated control tissue.

DETAILED DESCRIPTION

I. Definitions

Figure 1:
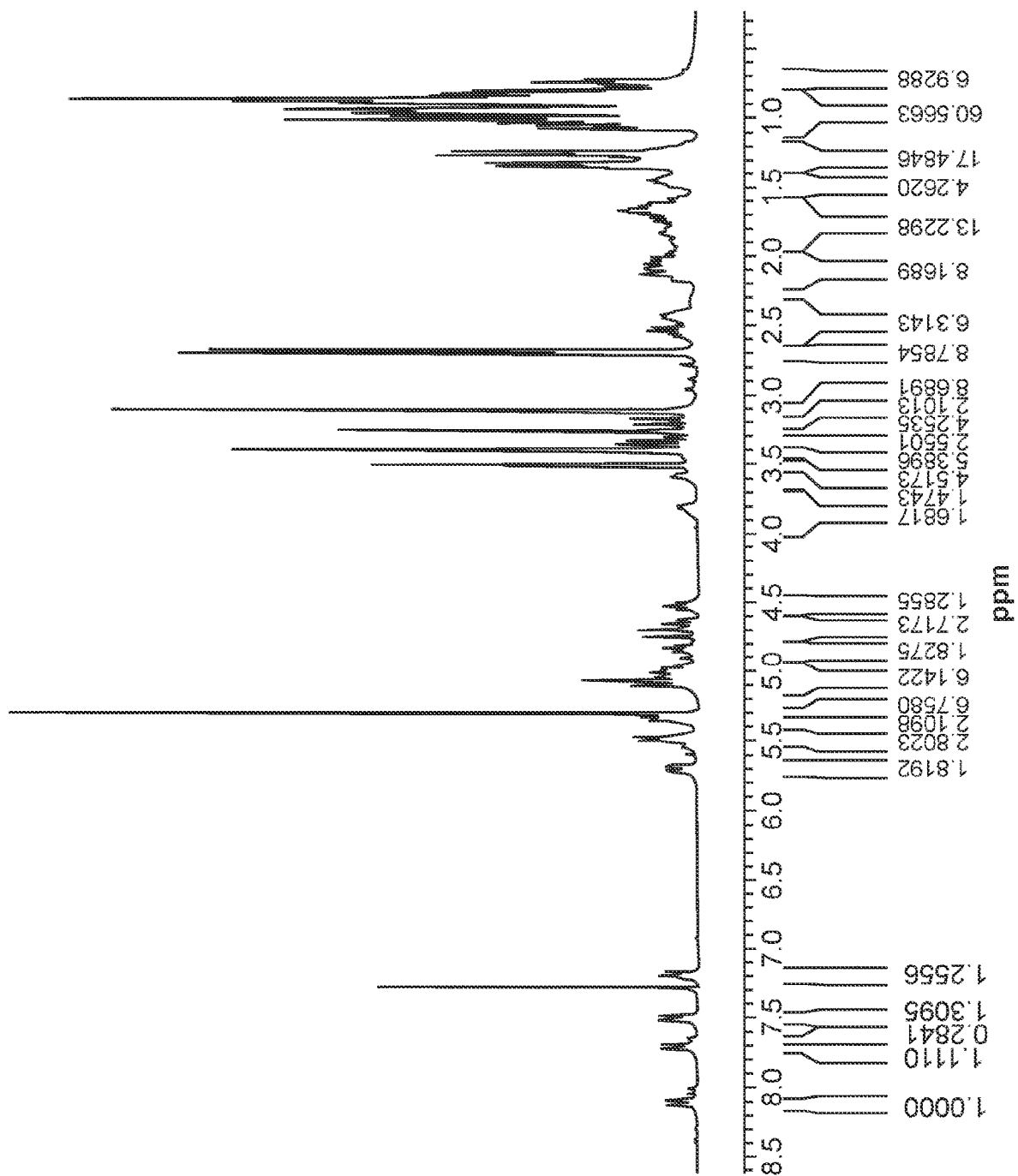
FIG. 1 is a $^1$H NMR (CDCl$_3$, 300 MHz) spectrum of compound B (Example 1).

The following terms are used herein, the definitions of which are provided for guidance.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. It will be understood by those of skill in the art that substituted groups of the present technology are chemically stable groups that allow isolation of the compounds in which they appear. Examples of substituent groups include: halogens (i.e., F, Cl, Br, and I); hydroxyls; alkoxy, carbonyls (oxo); carboxylates; esters; urethanes; oximes; hydroxylamines; alkoxyamines; thiols; sulfides; sulfoxides; sulfones; sulfonyls; sulfonamides; amines; azides; amides; nitro groups; nitriles (i.e., CN); and the like.

Alkyl groups include straight chain and branched chain alkyl groups having (unless indicated otherwise) from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like. In some embodiments the alkyl group is substituted with 1, 2, or 3 substituents.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$Cl$_3$)═CH$_2$, among others. Representative substituted alkenyl groups may be mono-substituted or substituted more than once, such as, but not limited to, mono-, di- or tri-substituted with substituents such as those listed above.

Heteroalkyl groups are alkyl groups (as defined herein) that include from 1 to 6 heteroatoms selected from N, O and S. It will be understood that each heteroatom present is bonded to at least one carbon atom within the heteroalkyl or heteroalkenyl group. In some embodiments the heteroalkyl groups include 1, 2, or 3 heteroatoms. Heteroalkyl groups may be substituted or unsubstituted. Examples of unsubstituted heteroalkyl groups include but are not limited to $CH=CH_2OCH_2$, $CH_3NHCH_2$, $CH_3CH_2N(CH_3)CH_2$, $CH_3CH_2SCH_2$, $CH_3CH_2OCH_2CH_2OCH_2CH_2$. Representative substituted heteroalkyl groups may be substituted one or more times with substituents such as those listed above (e.g., 1, 2 or 3 times), and include without limitation haloheteroalkyl (e.g., trifluoromethyloxyethyl), carboxyalkylaminoalkyl, and the like.

Groups described herein having two or more points of attachment (i.e., divalent, trivalent, or polyvalent) within the compound of the present technology are designated by use of the suffix, "ene." For example, divalent alkyl groups are alkylene groups, divalent heteroalkyl groups are heteroalkylene groups, and so forth. Substituted groups having a single point of attachment to the compound of the present technology are not referred to with the "ene" designation. Thus, e.g., chloroethyl is not referred to herein as chloroethylene.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10%4 of the particular term—for example, "about 1 kDa" would mean "0.9 kDa to 1.1 kDa."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Thus, for example, a group having 1-5 atoms refers to groups having 1, 2, 3, 4, or 5 atoms. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. Examples of tautomers include keto, enol, and enolate forms. The presence and concentrations of the isomeric forms will depend on the environment the compound is found in and may be different depending upon, for example, whether the compound is a solid or is in an organic or aqueous solution. Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The term "administering" a molecule to a subject means delivering the molecule to the subject. "Administering" includes prophylactic administration of the composition (i.e., before the disease and/or one or more symptoms of the disease are detectable) and/or therapeutic administration of the composition (i.e., after the disease and/or one or more symptoms of the disease are detectable). The methods of the present technology include administering one or more compounds. If more than one compound is to be administered, the compounds may be administered together at substantially the same time, and/or administered at different times in any order. Also, the compounds of the present technology may be administered before, concomitantly with, and/or after administration of another type of drug or therapeutic procedure (e.g., surgery).

The terms "alter" and "modify" when in reference to the level of any molecule (e.g., multidrug resistance protein 2 (MRP2), multidrug resistance protein 1 (MRP1), hepoxilin A3 ($HXA_3$) synthase, N-acyl ethanolamine (NAE), amino acid sequence, nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 ($HXA_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), refer to an increase and/or decrease.

"Cannabinoid receptor type 2" ("CB2") is a G protein-coupled receptor from the cannabinoid receptor family that in humans is encoded by the CNR2 gene. The principal endogenous ligand for the CB2 receptor is 2-arachidonoylglycerol (2-AG).

The term "conjugating," and grammatical equivalents, when made in reference to conjugating a molecule of interest and a polymer means covalently linking the molecule of interest to the polymer. Linkage may be direct, Alternatively, linkage may be indirect via a linking group or moiety. Methods for conjugation to polymers are known in the art, including methods for conjugation to a polypeptide to produce a fusion protein (Pasut, *Polymers* 6:160-178 (2014); Medscape, *Nanomedicine* 5(6):915-935 (2010)). In some embodiments, the conjugate is comprises cyclosporine A conjugated to a PEG polymer.

Use of the terms "comprising", "including" or similar terms to describe or define an embodiment of a compound, composition or method having one or more elements shall be understood to also disclose embodiments "consisting" or "consisting essentially" of the elements and vice versa. In other words, disclosure of embodiments open to elements beyond those listed ("comprising"), also are to be understood to disclose embodiments which are closed to additional elements ("consisting") or which may only include additional elements that do not materially affect the characteristics of the embodiment ("consisting essentially"). Likewise, embodiments consisting or consisting essentially of the listed elements shall be understood to disclose embodiments comprising those elements.

As used herein, the terms "effective amount" or "therapeutically effective amount," or "pharmaceutically effective amount" refer to a quantity sufficient to achieve a desired therapeutic and/or prophylactic effect, e.g., an amount which results in the full or partial amelioration of inflammation (e.g., inflammation associated with neutrophil migration into a target tissue) or disease or disorders or symptoms associated with inflammation in a subject in need thereof. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In some embodiments, multiple doses are administered. Additionally or alternatively, in some embodiments, multiple therapeutic compositions or compounds are administered. In the methods described herein, the therapeutic compounds may be administered to a subject having one or more signs or symptoms of a disease or disorder associated with inflammation (e.g., inflammation associated with increased neutrophil migration into a tissue).

"Endocannabinoids" ("ECs") are compounds that bind to the cannabinoid receptors, CB1 and CB2, as well as more recently described atypical receptors GPR55 and GPR119. The two main classes of eicosanoid-type ECs are "N-acylethanolamines" ("NAEs") and monoacylglycerols (MAGs), which are metabolized by fatty acid amide hydrolase (FAAH) and monoacyl glycerol lipase (MAGL), respectively. "N-acylethanolamine" is an endocannabinoid and is a type of fatty acid amide formed when one of several types of acyl group is linked to the nitrogen atom of ethanolamine. N-acylethanolamines are metabolized by fatty acid amide hydrolase (FAAH). Exemplary N-acylethanolamine endocannabinoids include ethanolamine, anandamide (AEA)(N-arachidonoylethanolamine), which is the amide of arachidonic acid (20:4 ω-6) oleoyl ethanolamide (OEA), and alpha-linolenoyl ethanolamide (α-LEA).

"Fatty acid amide hydrolase," "FAAH," and "EC 3.5.1.99" interchangeably refer to a member of the serine hydrolase family of enzymes. It was first shown to break down anandamide. In humans, it is encoded by the gene FAAH.

"Hepoxilin A3 synthase," "HXA$_3$ synthase," "ALOX12," "12-lipoxygenase," "arachidonate 12-lipoxygenase," "12S-Lipoxygenase," "12-LOX," and "12S-LOX" interchangeably refer to a lipoxygenase-type enzyme (i.e., an enzyme that catalyzes the deoxygenation of polyunsaturated fatty acids in lipids containing a cis,cis-1,4-pentadiene structure) that in humans is encoded by the ALOX12 gene, which is located along with other lipoxygenases on chromosome 17p13.3.

The term "increase" when in reference to a compound e.g., N-acylethanolamine, means increase the level and/or activity of N-acylethanolamine. The terms "increase," "elevate," "raise," and grammatical equivalents (including "higher," "greater," etc.) when in reference to the level of any molecule (e.g., multidrug resistance protein 2 (MRP2), multidrug resistance protein 1 (MRP1), hepoxilin A3 (HXA$_3$) synthase, N-acyl ethanolamine (NAE), amino acid sequence, and nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 (HXA$_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the compositions and/or methods of the present technology. In a further embodiment, the second sample (or the second subject) is exemplified by, but not limited to, a sample (or subject) that has not been manipulated using the compositions and/or methods of the present technology. In an alternative embodiment, the second sample (or the second subject) is exemplified by, but not limited to, a sample (or subject) that has been manipulated, using the compositions and/or methods of the present technology, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the compositions and/or methods of the present technology is sought to be determined on one sample (or subject). In another embodiment, the first and second samples (or subjects) may be different, such as when comparing the effect of the compositions and/or methods of the present technology on one sample (subject), for example a patient participating in a clinical trial and another individual in a hospital.

The term "inhibit" when used in reference to a compound, e.g., multidrug resistance protein 2 (MRP2), hepoxilin A3 (HXA$_3$) synthase, etc., means inhibit the activity and/or level of HXA$_3$. The terms "inhibit," "reduce," "diminish," "suppress," "decrease," and grammatical equivalents (including "lower," "smaller," etc.) when in reference to the level of any molecule (e.g., multidrug resistance protein 2 (MRP2), multidrug resistance protein 1 (MRP1), hepoxilin A3 (HXA$_3$) synthase, N-acyl ethanolamine (NAE), amino acid sequence, and nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 (HXA$_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of molecule, cell, and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the compositions and/or methods of the present technology. In a further embodiment, the second sample (or the second subject) is exemplified by, but not limited to, a sample (or subject) that has not been manipulated using the compositions and/or methods of the present technology. In an alternative embodiment, the second sample (or the second subject) is exemplified by, but not limited to, a sample (or subject) that has been manipulated, using the compositions and/or methods of the present technology, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the compositions and/or methods of the present technology is sought to be determined on one sample (or subject). In another embodiment, the first and second samples (or subjects) may be different, such as when comparing the effect of the compositions and/or methods of the present technology on one sample (subject), for example a patient participating in a clinical trial and another individual in a hospital.

"Multidrug resistance-associated protein 2," "multidrug resistance protein 2" ("MRP2"), "canalicular multispecific organic anion transporter 1" ("cMOAT"), "ATP-binding cassette sub-family C member 2" ("ABCC2") are interchangeably used to refer to protein that in humans is encoded by the ABCC2 gene.

"Multidrug resistance protein 1," "MRP1" and "ABCC1" are interchangeably used to refer to a uni-directional efflux transporter protein with a wide substrate specificity including important therapeutics. Some of the main roles of this transporter are: (i) efflux of xenobiotic and endogenous metabolites; (ii) transport of inflammatory mediators (e.g., LTC4); and (iii) defense against oxidative stress. The 190-kDa MRP1 has a core structure consisting of two transmembrane domains (TMD), each followed by a nucleotide binding domain (NBD). In common with MRP2, 3, 6, and 7, MRP1 contains a third TMD (TMD0) with five predicted trans membrane segments and an extra cytosolic NH$_2$ terminus connected to the core structure by a linker region (L0)(Rosenberg et al., *J. Biol. Chem.* 276(19):13076-16082 (2001)). The TMD0 appears to be important for MRP1 trafficking to the plasma membrane (Bakos et al., *J. Cell Sci.* 113(Pt24):4451-4461 (2000)), and the precise roles, mechanisms, and dependencies of TMD0 and L0 are the subject of significant research (Westlake et al. *Mol. Biol. Cell* 16(5): 2483-2492 (2005)). MRP1 has broad substrate specificity, transporting hydrophobic and anionic molecules, glucuronide and glutathione conjugates, as well as endogenous glutathione. Although many MRP1 substrates are conjugated to glutathione, co-transport of free glutathione is often observed, and appears to stimulate transport of e.g., vincristine and daunorubicin (Hooijberga et al., *FEBS Letters* 469:47-51(2000)). Glutathione itself is a low affinity substrate of MRP1 (Km=1-5 mM). Multiple allosterically cooperative, non-overlapping substrate-binding sites are postulated, which may explain why various substrates both cross-inhibit and cross-stimulate (Bakos et al., *Pflugers Arch— Eur. J Physiol* 453:621-641(2007)). The inflammatory cytokine LTC4 and its main metabolite LTD4 are some of the highest affinity MRP1 substrates, suggesting a key role for MRP1 in cytokine release from LTC4 producing cells. In fact, intracellular LTC4 accumulation was observed in mrp1 (−/−) mice (Robbiani et al., *Cell* 103:757-768 (2000)). Additionally, although viable, healthy, and fertile with normal phenotype, knockout mrp1 (−/−) mice were hypersensitive to cytotoxic drugs (Wijnholds et al., *Nat. Med.* 3:1275-1279 (1997)). MRP1 is exemplified by the human protein sequence NCBI Reference Sequence: NP_004987.2 encoded by the DNA sequence NCBI Reference Sequence: NG_028268.1. There are at least 15 naturally occurring mutations identified in MRP1, and many of them have been found to affect its in vitro transport activity. Polymorphisms and mutagenesis studies have been reviewed in He et al., *Curr. Med. Chem.* 18:439-481 (2011). Although many MRP1 SNPs are known, their incidence in populations is reported to be relatively low. In mainland Chinese populations the MRP1 polymorphism allelic frequencies of Cys43Ser (128G>C), Thr73Ile (218C>T), Arg723Gln (2168G>A) and Arg1058Gln (3173G>A) were 0.5%, 1.4%, 5.8% and 0.5%, respectively (Ji-Ye Yin et al., *Pharmacogenet. Genomics* 19(3):206-216 (2009)).

"P-glycoprotein" ("P-gp") is an efflux membrane transporter, and is responsible for limiting cellular uptake and the distribution of xenobiotics and toxic substances.

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

"Polymer" is a substance that has a molecular structure consisting chiefly or entirely of a large number of similar units bonded together. Polymers may occur naturally (e.g., cellulose, polypeptides, nucleotides sequences, etc.) or are artificial (e.g., plastics, resins, etc.). Polymers may be used as carriers of drugs to which they are conjugated, and may enhance the solubility of the conjugated drug, improve its pharmacokinetic profile, protect the drug against degradation, release the drug under certain conditions, such as change in pH or in the presence of enzymes, such as esterases, lipases or proteases. In addition, a targeting moiety or a solubilizer may also be introduced into the conjugate to boost its therapeutic index (Medscape, *Nanomedicine* 5(6):915-935(2010)). Polymers may also be utilized to restrict the distribution of the drug conjugated to it by, for example, preventing the conjugated drug from crossing into specific body compartments (e.g., from the gastrointestinal lumen to the underlying tissue). Polymers may be natural polymers and/or synthetic linear polymers, and include polyethylene glycol (PEG), dextran, periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide)(PLA/PLGA), poly(hydroxyalkylmethaacrylamide), polyglycerol, 25 polyamidoamine (PAMAM), polyethylenimine (PEI), and polypeptides.

"SipA" and "*Salmonella* T3SS effector protein" are used interchangeably to refer to a protein produced by *Salmonella*, as exemplified by the amino acid sequence of *Salmonella enterica* subsp. enterica serovar Typhimurium str. SL1344 (GenBank: AAA86618.1) encoded by the DNA sequence (Locus taq) SL1344_2861 of the *Salmonella enterica* subsp. enterica serovar Typhimurium str. SL1344, complete genome sequence (NCBI Reference Sequence: NC_016810.1). The SipA sequence is provided by WO 2015/089268.

"Target tissue" that may suffer from inflammation includes, without limitation, epithelial tissue, mucosal tissue, etc. Exemplary epithelial tissue and/or mucosal tissue include gastrointestinal, lung (e.g., bronchial tissue), liver, stomach, colon, brain, gallbladder, renal, female genital tract, ocular, urinary tract, etc., resulting in "inflammatory diseases" such as intestinal disease (exemplified by proctitis, orchitis, Crohn's disease, colitis (such as ulcerative colitis, also known as colitis ulcerosa), infectious/non-infectious enterocolitis, inflammatory bowel disease (IBD), etc.), inflammatory lung conditions (such as pneumococcal infection, asthma, chronic obstructive pulmonary disease (COPD), and pulmonary fibrosis), inflammatory skin diseases (such as dermatitis (eczema), rosacea, seborrheic dermatitis, and psoriasis), ocular disease (exemplified by uveitis, retinitis, keratitis, macular degeneration, etc.), urogenital disease (such as urinary tract infection), sexually transmitted diseases (such as pelvic inflammatory disease that includes inflammatory disease exemplified by gonorrhea infection and/or *chlamydia* infection, and by ulceration disease exemplified by herpes), urethritis, etc. As used herein, "target tissue" also encompasses an anatomic space, e.g., the intestinal lumen.

"Treating," "treat," "treated," or "treatment" as used herein covers the treatment of a disease or disorder described herein (e.g., inflammation), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. Symptoms may be assessed by methods known in the art, for example, biopsy and histology, and blood tests to determine relevant enzyme levels, metabolites or circulating antigen or antibody (or other biomarkers), quality of life questionnaires, patient-reported symptom scores, and imaging tests.

As used herein, "prevention" or "preventing" of a disorder or condition refers to a compound that, in a statistical sample, reduces the occurrence of the disorder or condition in the treated sample relative to a control sample, or delays the onset of one or more symptoms of the disorder or condition relative to the control sample.

It is also to be appreciated that the various modes of treatment or prevention of medical diseases and conditions as described are intended to mean "substantial," which includes total but also less than total treatment or prevention, and wherein some biologically or medically relevant result is achieved.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, ave, etc. In some embodiments, the mammal is murine. In some embodiments, the mammal is human.

A subject "in need" of treatment according to the methods and/or compositions of the present technology includes a subject that is "suffering" from inflammation (i.e., a subject that is experiencing and/or exhibiting one or more clinical and/or subclinical symptoms of inflammation), and a subject "at risk" of inflammation. A subject "in need" of treatment includes animal models of inflammation. Subject "at risk" of inflammation refers to a subject that is not currently exhibiting inflammation symptoms and is predisposed to expressing one or more symptoms of the disease. This predisposition may be based on family history, genetic factors, environmental factors such as exposure to detrimental compounds present in the environment, etc. It is not intended that the present technology be limited to any particular signs or symptoms. Thus, it is intended that the present technology encompass subjects that are experiencing any range of disease, from sub-clinical symptoms to full-blown inflammatory disease, wherein the subject exhibits at least one of the indicia (e.g., signs and symptoms) associated with the inflammatory disease.

"Substantially the same," "without substantially altering," "substantially unaltered," and grammatical equivalents, when in reference to the level of any molecule (e.g., multidrug resistance protein 2 (MRP2), multidrug resistance protein 1 (MRP1), hepoxilin A3 (HXA$_3$) synthase, N-acyl ethanolamine (NAE), amino acid sequence, nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 (HXA$_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) means that the quantity of molecule, cell, and/or phenomenon in the first sample (or in the first subject) is neither increased nor decreased by a statistically significant amount relative to the second sample (or in a second subject). Thus, in one embodiment, the quantity of molecule, cell, and/or phenomenon in the first sample (or in the first subject) is from 90% to 100% (including, for example, from 91% to 100%, from 92% to 100%, from 93% to 100%, from 94% to 100%, from 95% to 100%, from 96% to 100%, from 97% to 100%, from 98% to 100%, and/or from 99% to 100%) of the quantity in the second sample (or in the second subject).

As used herein, "weight percent" of a component, unless specifically stated to the contrary, is based on the total weight of the formulation or composition in which the component is included.

II. General

In one aspect, the present technology the present technology provides methods, compounds, and compositions for inhibiting formyl peptide receptor I (FPR1) and for treating disease associated with FPR1 activation. In some embodiments, disease associated with FPR1 activation comprises celiac disease.

In one aspect, the present technology provides methods, compounds, and compositions for treating neutrophil-mediated inflammation and disease associated with neutrophil-mediated inflammation. In particular, the present technology provides a method for treating neutrophil-mediated inflammation in a target tissue of a mammalian subject in need thereof, comprising administering to the subject a therapeutically effective amount of one or more first compound that increases the level and/or activity of multidrug resistance protein 1 (MRP1), wherein the therapeutic amount of the first compound reduces migration of neutrophils into the target tissue, and/or administering a therapeutically effective amount of one or more second compound that inhibits one or more of multidrug resistance protein 2 (MRP2), and hepoxilin A3 (HXA$_3$) synthase, wherein the therapeutic amount of the second compound reduces migration of neutrophils into the target tissue, and/or administering a therapeutically effective amount of one or more third compound that increases one or more N-acylethanolamines (NAEs), wherein the therapeutic amount of the third compound reduces migration of neutrophils into the target tissue.

In one embodiment, the present disclosure provides methods for treating neutrophil-mediated inflammation by targeting the pro-inflammatory MRP2/HXA$_3$ pathway, comprising administering to the subject a therapeutically effective amount of one or more compound that inhibits the activity and/or level of one or more of multidrug resistance protein 2 (MRP2) and hepoxilin A3 (HXA$_3$) synthase, wherein the therapeutic amount of the compound reduces migration of neutrophils into the target tissue.

In another embodiment, the present disclosure also provides methods for treating neutrophil-mediated inflammation by targeting the anti-inflammatory P-gp/endocannabinoid pathway, comprising administering to the subject a therapeutically effective amount of one or more compound that increases the level and/or activity of one or more N-acylethanolamines (NAEs), wherein the therapeutic amount of the compound reduces migration of neutrophils into the target tissue.

In a further embodiment, the present disclosure further provides methods for treating neutrophil-mediated inflammation, comprising administering to the subject a therapeutically effective amount of one or more second compound that increases the level and/or activity of multidrug resistance protein 1 (MRP1), wherein the therapeutic amount of the compound reduces migration of neutrophils into the target tissue In yet another embodiment, the present disclosure provides methods for treating neutrophil-mediated inflammation by targeting both the anti-inflammatory P-gp/endocannabinoid, and the pro-inflammatory MRP2/HXA$_3$ pathway, the method comprising administering to the subject a therapeutically effective amount of (A) one or more first compound that inhibits the activity and/or level of one or more of multidrug resistance protein 2 (MRP2) and hepoxilin A3 (HXA$_3$) synthase, and (B) one or more second compound that increases the level and/or activity of one or more N-acylethanolamines (NAEs), wherein the therapeutic amount of the first and second compounds reduces migration of neutrophils into the target tissue.

III. Compounds of the Present Technology

The present technology provides compositions for treating neutrophil-mediated inflammation and conditions associated therewith. In some embodiments, the present technology provides compositions comprising one or more of a first compound that increases the level and/or activity of multidrug resistance protein 1 (MRP1), a second compound that inhibits one or more of multidrug resistance protein 2 (MRP2) and hepoxilin A3 (HXA$_3$) synthase, and/or a third compound that increases one or more N-acylethanolamines (NAEs).

In some embodiments, the present technology discloses a cyclosporine A-PEG conjugate defined by formula I:

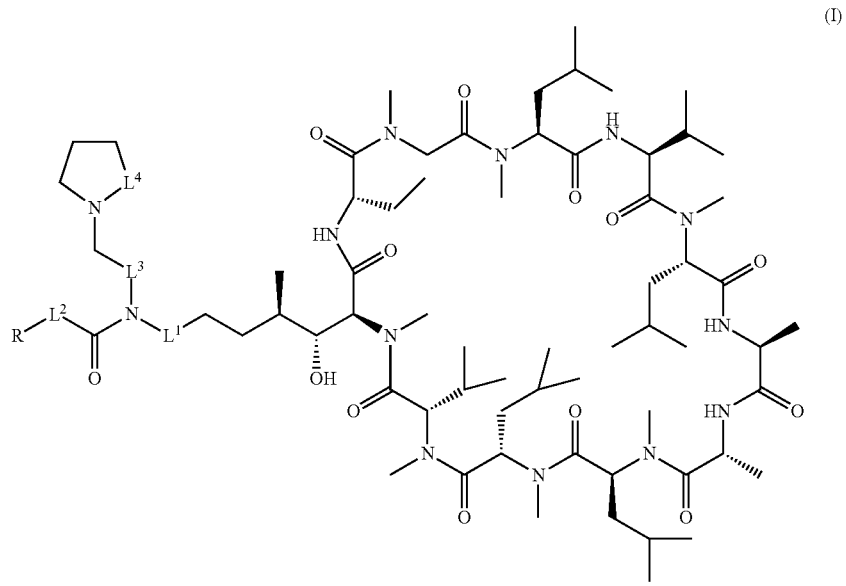

(I)

a stereoisomer thereof, or a pharmaceutically acceptable salt of the foregoing. In formula I, $L^1$ may be a $C_{1-6}$ alkylene group optionally substituted with one or more F. For example, in some embodiments, L may be methylene, ethylene, propylene, butylene, pentylene, or hexylene. In some embodiments, $L_1$ may be a $C_{1-4}$ alkylene group, such as a propylene group, e.g., n-propylene. In some embodiments, $L_1$ may be $C_{1-6}$ fluoroalkyl group. The fluoroalkyl group may have 1, 2, 3, 4 or more F and/or may be perfluorinated.

In Formula I, $L^2$ is absent or is a linker selected from O, NH, or a $C_{1-12}$ alkylene or heteroalkylene group. In some embodiments $L^2$ may be absent. In some embodiments, $L^2$ may be a $C_{1-12}$ alkylene or even a $C_{1-6}$ alkylene. For example, in some embodiments, $L^2$ may be methylene, ethylene, propylene, butylene, pentylene, or hexylene. In some embodiments, $L^2$ may be methylene. In some embodiments, $L^2$ may be a $C_{1-12}$ heteroalkylene group or a $C_{1-6}$ heteroalkylene group. The heteroalkylene may contain one, two or three O, S or NH groups or any combination thereof. In some embodiments, the heteroalkylene may have one or two NH groups, e.g. ($C_1$-$C_{12}$ alkylene)-NH (e.g., $CH_2CH_2NH$, $CH_2CH_2CH_2NH$, $CH_2CH_2CH_2CH_2NH$, $CH_2CH(CH_3)CH(CH_3)CH_2NH$), ($C_n$ alkylene)NH($C_p$ alkylene) where n, p are independently an integer from 1-10, but n+p does not exceed 12 (e.g., $CH_2CH_2CH_2NHCH_2CH_2$), NH—($C_1$-$C_{10}$ alkylene)NH (e.g., $NH(CH_2)_5NH$, $NH(CH_2)_6NH$, $NH(CH_2)_8NH$), or $NH(C_u$ alkylene)NH($C_p$ alkylene) where n and p are integers as defined previously (e.g., $NHCH_2CH_2CH_2NH$ $CH_2CH_2$, $NH(CH_2)_6NHCH_2$). In some embodiments, the $L^2$ may be a heteroalkylene that contains one or two oxygen atoms, including but not limited to ($C_1$-$C_{10}$ alkylene)-O (e.g., $CH_2CH_2O$, $CH_2CH_2CH_2O$, $CH_2CH_2CH_2CH_2O$, $CH_2CH(CH_3)CH(CH_3)CH_2O$), ($C_n$ alkylene)O($C_p$ alkylene) where n, p are independently an integer from 1-10, but n+p does not exceed 12 (e.g., $CH_2CH_2CH_2OCH_2CH_2$), O—($C_1$-$C_{10}$ alkylene)O (e.g., $O(CH_2)_5O$, $O(CH_2)_6O$, $O(CH_2)_8O$), or $O(C_n$ alkylene)O($C_p$ alkylene) where n and p are integers as defined previously (e.g., $OCH_2CH_2CH_2O$ $CH_2CH_2$, $O(CH_2)_6$ $OCH_2$). In some embodiments, $L^2$ may be a heteroalkylene containing an O and an NH group, including but not limited to NH—($C_1$-$C_{10}$ alkylene)O, (e.g., $NH(CH_2)_5O$, $NH(CH_2)_6O$, $NH(CH_2)_8O$), or $NH(C_n$ alkylene)O($C_p$ alkylene) where n and p are integers as defined previously (e.g., $NHCH_2CH_2OCH_2CH_2$, $O(CH_2)_6NHCH_2$).

In Formula I, $L^3$ is a $C_{1-6}$ alkylene group. For example, in some embodiments, $L^3$ may be methylene, ethylene, propylene, butylene, pentylene, or hexylene. In some embodiments, $L^3$ may be methylene.

In Formula I, $L^4$ is a methylene or ethylene group. It will be appreciated that when $L^4$ is methylene, the compound of Formula I contains a pyrrolidinyl group. When $L^4$ is ethylene, the compound of Formula I contains a piperidinyl group.

In Formula I, R is a polyethylene glycol (PEG) group. In some embodiments, R is a PEG terminated with OH or a $C_{1-6}$ alkoxy group, e.g., methoxy, ethoxy, propyloxy, etc. In some embodiments, R is a PEG terminated with OH or $C_{1-3}$ alkoxy group. In some embodiments, R is a PEG terminated with OH or a methoxy group. In some embodiments, the PEG may have various number of ethylene oxide subunits, e.g., 2-500, 10-500, 10-400, 10-300, 10-200, 10-100, 25-75, 30-60, or 40-50 ethylene oxide subunits, e.g., 40, 41, 42, 43, 44, 45, 46, 47, 48, 49 or 50 ethylene oxide subunits or a range between and including any two of the foregoing values.

Thus, the PEG can have a wide range of molecular weight. In some embodiments, the PEG has a weight average molecular weight in the range of about 100 Da to about 20 kDa. In some embodiments the polymer has a weight average molecular weight in the range of about 1 kDa to about 20 kDa. In some embodiments, the PEG has a weight average molecular weight less than 1 kDa. In some embodiments, the PEG has a weight average molecular weight less than 10 kDa. In some embodiments, the weight average molecular weight of the PEG is about 1 kDa, 2 kDa, 5 kDa, 10 kDa, 15 kDa, 20 kDa, or any range between and including two of these values, e.g., about 1 kDa to about 5 kDa. In some embodiments, R is a PEG having a weight average molecular weight of about 2 kDa. It is within the skill in the art to determine weight average molecular weight of PEG by, e.g., gel permeation chromatography.

The PEGs described herein can have a number of different geometries. For example, in some embodiments, the PEGs are linear polymers, branched polymers, forked polymers, or a combination of any of these geometries. In some embodiments, the PEG is linear.

The cyclosporine A-PEG (CSA-PEG) conjugates may be prepared using standard techniques known in the art. In some embodiments, the alkene containing side-chain of the Me-BMt residue of cyclosporine A is subjected to a Grubb's metathesis reaction with a haloalkene (e.g., 4-bromobut-1-ene) to convert the sidechain into a haloalkenyl group available for further modification. The cyclic amine may be introduced into the modified CSA by a standard nucleophilic displacement reaction of e.g., pyrrolidinyl alkylamine or piperidinyl alkylamine with the halo group in the presence of a suitable base. If desired, the alkene may be hydrogenated to provide a fully saturated side chain using hydrogen and a suitable transition metal catalyst (e.g., Pd/C, Pt, etc.). PEG groups of various lengths may be installed using, a suitable derivative having a linking group capable for forming a single covalent linkage (e.g., a functional group such as carboxyl, aldehyde, etc.) whereas any other functional groups are masked or protected. For example, a PEG having an alkoxy terminus and a carboxyl terminus may be coupled to the modified CSA in the presence of a coupling agent (e.g., DCC, EDC/HOBt, etc.) to provide the tertiary amide linkage of Formula I. Alternatively, an active ester, mixed anhydride or acid halide derivative of PEG may be prepared and reacted with the modified CSA. (See, for example, Bodansky, M. & Bodanszky, A., *The Practice of Peptide Synthesis*, Springer-Verlag, New York, 1984.) Variations of this synthetic scheme using different PEGS and PEG derivative will be readily appreciated by those of skill in the art.

In some embodiments, compounds of the present technology are used in combination with one or more compounds that increase (multidrug resistance protein 1) MRP1 for the treatment of inflammatory disease. In some embodiments, increased levels of MRP1 are achieved by transfection of mRNA sequences that encode MRP-1, using viral vectors carrying a MRP-1 gene insert under a tissue specific promoter (Hao et al., *Cancer Biology & Therapy*, 5(3):261-266, DOI: 10.4161/cbt.5.3.2381), using small molecules such as Ivermectin (STROMECTOL®)(Raza et al., *Parasites & Vectors* 9:522, DOI: 10.1186/s13071-016-1806-9 (2016)), and such as anti-cancer drugs. Numerous chemotherapeutic agents, including, but not limited to, doxorubicin and vinblastine have been reported to induce MRP1 expression, and a role for nuclear hormone regulation via CAR has been reported (Bakos et al., *Pflugers Arch—Eur J Physiol* 453:621-641 (2007)).

In some embodiments, compounds of the present technology are used in combination with one or more multidrug resistance protein 2 (MRP2) inhibitors for the treatment of inflammatory disease. In some embodiments, the MRP2 inhibitor is selected from the group consisting of MRP2 RNAi; 3-([3-(2-[7-chloro-2-quinolinyl]ethenyl)phenyl-(3-dimethylamino-3-oxopropyl)-thio-methyl]thio)propanoic acid (also known as "MK571" and CysLT1 (LTD4) leukotriene receptor inverse agonist)(Tocris, Minneapolis, USA) (Genuuso et al. (2004) PNAS 101:2470-2475); Probenecid (also known as "PROBALANT™"), exemplified by probenecid inhibition of MRP2; FUROSEMIDE®; RITONAVIR®; SAQUINAVIR®; LAMIVUDINE®; ABACAVIR®; EMTRICITABINE®; EFAVIRENZ®; DELAVIRDINE®; NEVIRAPINE®; CIDOFOVIR®; ADEFOVIR®; and TENOFOVIR®. In some embodiments, the compound is conjugated to a polymer.

In some embodiments, the compound that inhibits the MRP2 comprises one or more of a compound that inhibits Hepoxilin A3 synthase, such as Hepoxilin A3 synthase RNAi. In some embodiments, the compound is conjugated to a polymer.

In some embodiments, the compound that inhibits the MRP2 comprises one or more compounds that inhibit fatty acid amide hydrolase (FAAH), such as FAAH RNAi; FAAH Inhibitor I (PubChem CID: 295380) 4-phenylmethoxyphenyl)N-butylcarbamate); URB597 (PubChem CID: 1383884) 3'-Carbamoyl-[1,1'-biphenyl]-3-yl cyclohexylcarbamate; FAAH inhibitor 1 (PubChem CID: 1190414)N-(4-(6-methylbenzo[d]thiazol-2-yl)phenyl)-1-(thiophen-2-ylsulfonyl) piperidine-4-carboxamide; FAAH Inhibitor, 2l (PubChem CID:71699786); FAAH Inhibitor, 2i (PubChem CUD: 71699785)N-Cyclohexylcarbamic acid 4-(dimethylamino)-3-phenylphenyl ester; FAAH inhibitor. 2h (PubChem CID: 71699784)N-Cyclohexylcarbamic acid 4-(hydroxymethyl)-3-phenylphenyl ester; FAAH Inhibitor, 2j (PubChem CID: 58801136); FAAH Inhibitor, 2e (PubChem CID: 58801135); FAAH Inhibitor, 2a (PubChem CID: 58801134); FAAH Inhibitor, 2b (PubChem CID: 58801129); FAAH Inhibitor, 2f (PubChem CID: 58801126) Carbamic acid, cyclohexyl-, 6-methyl[1,1'-biphenyl]-3-yl ester; FAAH Inhibitor. 2k (PubChem CID: 58801125); FAAH Inhibitor, 2c (PubChem CID: 57582480); FAAH Inhibitor, 2g (PubChcm CID: 44626363); FAAH Inhibitor, 2d (PubChem CID: 44626362); AM374, palmitylsulfonyl fluoride; ARN2508, derivative of flurbiprofen; BIA 10-2474; BMS-469908; CAY-10402; JNJ-245; JNJ-1661010; JNJ-28833155; JNJ-40413269; JNJ-42119779; JNJ-42165279; LY-2183240; Cannabidiol; MK-3168; MK-4409; MM-433593; OL-92; OL-135; PF-622; PF-750; PF-3845; PF-04457845; PF-04862853; RN-450; SA-47; SA-73; SSR-411298; ST-4068; TK-25; URB524; URB597 (KDS-4103, Kadmus Pharmaceuticals); URB694; URB937; VER-156084; V-158866; and Multiple FAAH inhibitors from ChemCruz® Biochemicals, Dallas, Texas). In some embodiments, the compound is conjugated to a polymer.

In some embodiments, the compound that inhibits the MRP2 comprises one or more compounds that inhibit P-glycoprotein (P-gp), such as P-gp RNAi; SipA; and small molecules (e.g., zosuquidar trihydrochloride (LY335979); VALSPODAR® (PSC833) (Inhibitor of P-gp-mediated MDR); CP 100356 hydrochloride (Sigma-Aldrich); and Elacridar hydrochloride (R & D Systems). See also, WO 2004071498 A1; WO 2014106021 A1; WO 2005033101 A1; WO 2004009584 A1: WO 2002030915 A2; US 20100029755 A1; and US 20060073196 A1). In some embodiments, the compound is conjugated to a polymer.

In some embodiments, cyclosporine A compounds of the present technology are used in combination with one or more compounds that increase N-acylethanolamines (NAEs) for the treatment of inflammatory disease. In some embodiments, the compound that increases NAEs is a cannabinoid receptor type 2 (CB2)"agonist" (i.e., a compound that specifically binds to, and activates, CB2). Illustrative CB2 agonists include GW-405,833; AM-1241; HU-308; JWH-015; JWH-133; L-759,633; L-759,656; beta-caryophyllene; arachidonylcyclopropylamide; and arachidonyl-2'-chloroethylamine. In some embodiments, the compound is conjugated to a polymer.

IV. Use of the Compositions of the Present Technology

The present technology provides methods for treating, preventing, or ameliorating neutrophil-mediated inflammation in a target tissue of a mammalian subject in need thereof, comprising administering to the subject a therapeutically effective amount of one or more first compound that inhibits one or more of multidrug resistance protein 2 (MRP2) and hepoxilin A3 (HXA$_3$) synthase, wherein the therapeutically effective amount of the first compound reduces migration of neutrophils into the target tissue. In some embodiments, the first compound is a cyclosporine A conjugate. In some embodiments, the method further comprises administering to the subject a therapeutically effective amount of one or more second compound that increases one or more N-acylethanolamines (NAEs), wherein the therapeutic amount of the second compound reduces migration of neutrophils into the target tissue. In a further embodiment, the method further comprises administering to the subject a therapeutically effective amount of one or more second and/or third compound that increases the level and/or activity of multidrug resistance protein 1 (MRP1), wherein the therapeutic amount of one or more second and/or third compound reduces migration of neutrophils into the target tissue. In another embodiment, the compounds of the present technology are administered singly or in any combination to a topical surface of the target tissue and/or at a luminal surface of the target tissue. In a further embodiment, the first compound that reduces migration of neutrophils into the target tissue is conjugated to a polymer. In another embodiment, the inflammation is non-infectious and/or infectious inflammation.

The present technology also provides methods for treating, ameliorating, or preventing neutrophil-mediated inflammation in a target tissue of a mammalian subject in need thereof, comprising administering to the subject a therapeutically effective amount of one or more first compound that increases one or more N-acylethanolamines (NAEs), wherein the therapeutic amount of the first compound reduces migration of neutrophils into the target tissue. In one embodiment, the method further comprises administering to the subject a therapeutically effective amount of one or more second compound that inhibits one or more of multidrug resistance protein 2 (MRP2) and HXA$_3$ synthase, wherein the therapeutic amount of the second compound reduces migration of neutrophils into the target tissue. In some embodiments, the second compound is a cyclosporine A conjugate. In another embodiment, the method further comprises administering to the subject a therapeutically effective amount of one or more second and/or third compound that increases the level and/or activity of multidrug resistance protein 1 (MRP1), wherein the therapeutic amount of the one or more second and/or third reduces migration of neutrophils into the target tissue. In a further embodiment, the one or more first compound that increases the one or more NAEs is a cannabinoid receptor type 2 (CB2) agonist. In another embodiment, the first compound that reduces migration of neutrophils into the target tissue is conjugated to a polymer.

In one aspect, the methods, compounds and compositions of the present technology relate to cyclosporine A-PEG conjugates defined by Formula I as well as stereoisomers thereof, and pharmaceutically acceptable salts of the foregoing:

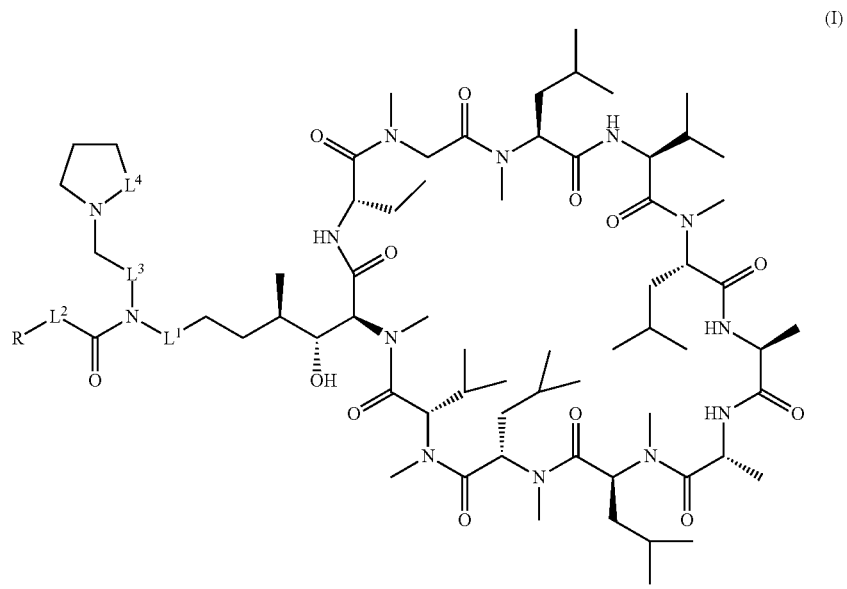

(I)

wherein L$^1$, L$^2$, L$^3$, L$^4$ and R may be as defined herein, as well as the use of one or more of these conjugates (including but not limited to a compound of Formula IA and BT117) to treat, ameliorate, or prevent neutrophil-mediated inflammation in a target tissue in a subject in need thereof. In other embodiments, the cyclosporine A conjugates in combination with one or more compounds (e.g., a compound that increases the level and/or activity of MRP1, or a compound that increases NAEs) will show a synergistic effect in this regard.

In some embodiments, the methods, compounds and compositions of the present technology relate to the use of one or more of the cyclosporine A conjugates of Formula I to treat, ameliorate, or prevent inflammatory bowel disease (IBD), such as ulcerative colitis (UC), Crohn's disease (CD), and infectious/non-infectious enterocolitis. In other embodiments, the cyclosporine A conjugates in combination with one or more compounds (e.g., a compound that increases the level and/or activity of MRP1, or a compound that increases NAEs) will show a synergistic effect in this regard.

In some embodiments, the methods and compostions of the present technology relate to the use of one or more of the cyclosporine A conjugates of Formula I to treat, ameliorate, or prevent infectious and non-infectious inflammatory lung conditions, including, but not limited to, pneumococcal infection, asthma, chronic obstructive pulmonary disease (COPD), and pulmonary fibrosis. In other embodiments, the cyclosporine A conjugates in combination with one or more compounds (e.g., a compound that increases the level and/or activity of MRP1, or a compound that increases NAEs) will show a synergistic effect in this regard.

In some embodiments, the methods, compounds and compositions of the present technology relate to the use of one or more of the cyclosporine A conjugates of Formula I to treat, ameliorate, or prevent inflammatory skin diseases including, but no limited to, dermatitis (eczema), rosacea, seborrheic dermatitis, and psoriasis. In other embodiments, the cyclosporine A conjugates in combination with one or more compounds (e.g., a compound that increases the level and/or activity of MRP1, or a compound that increases NAEs) will show a synergistic effect in this regard.

The methods of the present technology are useful for treating "inflammation," which is a localized physical condition in which part of the body reacts to injury and/or infection. The classic symptoms of inflammation are heat, redness, swelling, pain, and/or loss of function. These are manifestations of the physiologic changes that occur during the inflammatory process. The three major components of this process are: (1) changes in the caliber of blood vessels and the rate of blood flow through them (hemodynamic changes); (2) increased capillary permeability; and (3) leukocytic exudation. "Neutrophil-mediated inflammation" refers to the leukocytic exudation and stage of inflammation, in which neutrophils move to the endothelial lining of the small blood vessels (margination) and line the endothelium in a tightly packed formation (pavementing). Eventually, these neutrophils move through the endothelial spaces and escape into the extravascular space (emigration). Once they are outside the blood vessels they are free to move and, by chemotaxis, are drawn to the site of injury. Accumulations of neutrophils (and macrophages) at the area of inflammation act to neutralize foreign particles by phagocytosis.

Inflammation includes acute inflammation, which is usually of sudden onset, marked by the classical signs of heat, redness, swelling, pain, and loss of function, and in which vascular and exudative processes predominate; catarrhal inflammation, which is a form affecting mainly a mucous surface, marked by a copious discharge of mucus and epithelial debris; chronic inflammation, which is prolonged and persistent inflammation marked chiefly by new connective tissue formation; it may be a continuation of an acute form or a prolonged low-grade form; interstitial inflammation, which is inflammation affecting chiefly the stroma of an organ; traumatic inflammation, which is one that follows a wound or injury; ulcerative inflammation, in which necrosis on or near the surface leads to loss of tissue and creation of a local defect (ulcer).

Inflammation may be infectious and/or non-infectious. "Infectious" inflammation refers to inflammation that is associated with and/or is caused by the invasion and multiplication of microorganisms such as bacteria, viruses, and parasites that are not normally present within the body. In contrast, "non-infectious" inflammation refers to inflammation that is not associated with and/or is not caused by the invasion and multiplication of microorganisms such as bacteria, viruses, and parasites that are not normally present within the body.

In another embodiment, the present technology provides a method for treating neutrophil-mediated inflammation by targeting the pro-inflammatory MRP2/HXA$_3$ pathway. In a particular embodiment, this method for treating neutrophil-mediated inflammation in a target tissue of a mammalian subject in need thereof, comprises administering to the subject a therapeutically effective amount of one or more first compound that inhibits the activity and/or level of one or more of multidrug resistance protein 2 (MRP2) and hepoxilin A3 (HXA$_3$) synthase, wherein the therapeutic amount of the first compound reduces migration of neutrophils into the target tissue. In some embodiments, the compound is a cyclosporine A conjugate.

In various embodiments, suitable in vitro or in vivo assays are performed to determine the effect of a specific composition of the present technology and whether its administration is indicated for treatment. In various embodiments, in vitro assays can be performed with representative cell-based assays, such as the neutrophil migration assay. In other embodiments, in vivo models, typified by animal models, may be used to determine if a given cyclosporine A conjugate alone or in combination with one or more additional compounds (e.g., an additional compound that inhibits one or more of MRP2 nd HXA$_3$ synthase, a compound that increases the level and/or activity of MRP1, or a compound that increases NAEs), exerts the desired effect in treating a disease or condition. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the an can be used prior to administration to human subjects.

In some embodiments, the methods of the present technology further comprise administering one or more antibiotic and/or anti-inflammatory agent. Examples of antibiotic/anti-inflammatory agents used singly or in combination in the methods of the present technology include, but are not limited to Dalbavancin (DALVANCE©, XYDALBA©), Oritavancin (ORBACTIVE©) Daptomycin (Cubicin©), Tedizolid (SIVEXTRO©), Ceftobiprole (ZEVTERA©, MABELIO©), Ceftolozane-tazobactam (ZERBAXA©) mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, flurandrenolone, fluclorolone acetonide, fludrocortisone, flumethasone pivalate, fluosinolone acetonide, fluocinonide, fluocortin butylester, fluocortolone, fluprednidene (fluorenylidene)acetate, flurandrenolone, halcinonide, hydrocortisone acetate, hydrocortisone butyrate, methylprednisolone, triamcinolone acetonide, cortisone, cortodoxone, fluocinonide, fludrocortisone, diflorasone diacetate, flurandrenolone acetonide, medrysone, amciafel, amcinafide, betamethasone, chloroprednisone, chloroprednisone acetate, clocortolone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, betamethasone dipropionate, triamcinolone, non-steroidal agents such as COX inhibitors. LOX inhibitors, p38 kinase inhibitors, immunosuppressant agents such as cyclosporin, and cytokine synthesis inhibitors, tetracycline, minocycline, and doxycycline, or any combination thereof.

In some embodiments, the methods of the present technology further comprise administering one or more antibodies, such antibodies targeting one or more of Clostridium difficile toxins, tumor necrosis factor (TNF), interleukins, metalloproteinase-9 (such as the antibody GS-5745, Gilead).

For example, in Crohn's disease, it may be desirable that anyone of the methods of the present technology further comprise administering one or more mesalamine products, corticosteroid formulations, both conventional corticosteroids and ileal-release budesonide, glucocorticosteroids/EEN immunomodulatives (such as azathioprine, 6-mercaptopurine, and methotrexate), anti-tumor necrosis factor (TNF) drugs (such as infliximab (Remicade, Janssen), adalimumab (Humira, AbbVie), and certolizumab pegol (Cimzia, UCB)), the anti-alpha-4 beta-7 integrin antibody vedolizumab (Entyvio, Takeda), the JAK inhibitors ABT-494 (AbbVie), and filgotinib (GLPG0634. Galapagos and Gilead)(Sandborn. The Present and Future of Inflammatory Bowel Disease Treatment Gastroenterology & Hepatology, Volume 12, Issue 7, July 2016).

For ulcerative colitis, it may be desirable that any one of the methods of the present technology further comprise administering one or more of 5-aminosalicylates, mesalamine, conventional corticosteroids or multimatrix budesonide (Uceris, Salix), which delivers the drug to the colon, azathioprine, 6-mercaptopurine, anti-TNF drugs (such as infliximab, adalimumab, and golimumab (Simponi, Janssen)), vedolizumab, Janus kinase (JAK) inhibitors (e.g., Tofacitinib (Xeljanz, Pfizer) ABT-494 (AbbVie), and filgotinib (GLPG0634, Galapagos and Gilead))(Sandborn 2016).

V. Combination Therapies

In some embodiments, the cyclosporine A conjugates of the present technology may be combined with one or more additional therapeutic agents for the prevention, amelioration, or treatment of a disease or condition.

In one embodiment, an additional therapeutic agent is administered to a subject in combination with a cyclosporine A conjugate of the present technology such that a synergistic therapeutic effect is produced.

In some embodiments, the cyclosporine A conjugates of the present technology are combined with one or more methods or compounds for the treatment or prevention of celiac disease or symptoms associated with celiac disease. In some embodiments, the one or more compounds comprises an anti-inflammatory agent. In some embodiments, the one or more compounds comprises infliximab. In some embodiments, one or more methods comprises a gluten-free diet.

In some embodiments, the cyclosporine A conjugates of the present technology are combined with one or more compounds that increase levels of multidrug resistance protein 1 (MRP1) described above.

In some embodiments, the cyclosporine A conjugates of the present technology are combined with one or more additional compounds that inhibit one or more of multidrug resistance protein 2 (MRP2) and hepoxilin A3 (HXA$_3$) synthase described above.

In some embodiments, the cyclosporine A conjugates of the present technology are combined with one or more additional compounds that increase N-acylethanolamines (NAEs) described above.

In some embodiments, the cyclosporine A conjugates of the present technology are combined with one or more additional therapeutic agents for treating neutrophil-mediated inflammation and conditions associated therewith, including, but not limited to, ulcerative colitis and Crohn's disease. In some embodiments, the present technology provides compositions comprising one or more of a first compound that increases the level and/or activity of multidrug resistance protein 1 (MRP1), a second compound, such as a cyclosporine A conjugate, that inhibits one or more of multidrug resistance protein 2 (MRP2) and hepoxilin A3 (HXA$_3$) synthase, and/or a third compound that increases one or more N-acylethanolamines (NAEs).

The multiple therapeutic agents (e.g., cyclosporine A conjugates, compounds that increase the level and/or activity of MRP1, additional inhibitors of MRP2 and HXA$_3$ synthase, and/or compounds that increase NAEs) may be administered in any order or even simultaneously. If simultaneously, the multiple therapeutic agents may be provided in a single, unified form, or in multiple forms (by way of example only, either as a single formulation or as two separate formulations). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

In some embodiments, the methods of the present technology further comprise administering to the subject a therapeutically effective amount of at least one compound that increases the level and/or activity of one or more N-acylethanolamines (NAEs), wherein the therapeutic amount of the compound reduces migration of neutrophils into the target tissue.

In some embodiments, the compound that increases NAEs is a cannabinoid receptor type 2 (CB2) "agonist" (i.e., a compound that specifically binds to, and activates, CB2). CB2 agonists are exemplified by GW-405,833; AM-1241; HU-308; JWH-015; JWH-133; L-759,633; L-759,656; beta-caryophyllene; arachidonylcyclopropylamide; and arachidonyl-2'-chloroethylamide.

In some embodiments, the methods of the present technology may further comprise administering one or more antibiotic and/or anti-inflammatory agent. Examples of antibiotic/anti-inflammatory agents used singly or in combination in the methods of the present technology include, but are not limited to Dalbavancin (DALVANCE©, XYDALBA©), Oritavancin (ORBACTIVE©) Daptomycin (Cubicin©), Tedizolid (SIVEXTRO©), Ceftobiprole (ZEVTERA©, MABELIO©), Ceftobiprole (ZEVTERA©, MABELIO©), Ceftolozane-tazobactam (ZERBAXA©) mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, flurandrenolone, fluclorolone acetonide, fludrocortisone, flumethasone pivalate, fluosinolone acetonide, fluocinonide, fluocortin butylester, fluocortolone, fluprednidene (fluorenylidene)acetate, flurandrenolone, halcinonide, hydrocortisone acetate, hydrocortisone butyrate, methylprednisolone, triamcinolone acetonide, cortisone, cortodoxone, fluocinonide, fludrocortisone, diflorasone diacetate, flurandrenolone acetonide, medrysone, amciafel, amcinafide, betamethasone, chloroprednisone, chloroprednisone acetate, clocortolone, clescinolone, dichlorisone, diflupredate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppressant agents such as cyclosporin, and cytokine synthesis inhibitors, tetracycline, minocycline, and doxycycline, or any combination thereof.

In some embodiments, the methods of the present technology may further comprise administering one or more antibodies, such as antibodies targeting one or more of *Clostridium difficile* toxins, tumor necrosis factor (TNF), interleukins, metalloproteinase-9 (such as the antibody GS-5745, Gilead).

In some embodiments, the present disclosure encompasses methods for the treatment, amelioration, or prevention of Crohn's disease, comprising administering one or more compounds of the present technology in combination with at least one or more mesalamine products, corticosteroid formulations, both conventional corticosteroids and ileal-release budesonide, glucocorticosteroids/EEN immunomodulatives (such as azathioprine, 6-mercaptopurine, and methotrexate), anti-tumor necrosis factor (TNF) drugs (such as infliximab (Remicade, Janssen), adalimumab (Humira, AbbVie), and certolizumab pegol (Cimzia. UCB)), the anti-alpha-4 beta-7 integrin antibody vedolizumab (Entyvio, Takeda), the JAK inhibitors ABT-494 (AbbVie), and filgotinib (GLPG0634, Galapagos and Gilead)(Sandborn, *Gastroenterology & Hepatology* 12(7)(2016)).

In some embodiments, the present disclosure encompasses methods for the treatment, amelioration, or prevention of ulcerative colitis, comprising administering one or more compounds of the present technology in combination with at least one or more of 5-aminosalicylates, mesalamine, conventional corticosteroids or multimatrix budesonide (Uceris, Salix), which delivers the drug to the colon, azathioprine, 6-mercaptopurine, anti-TNF drugs (such as infliximab, adalimumab, and golimumab (Simponi, Janssen)), vedolizumab, Janus kinase (JAK) inhibitors (e.g., Tofacitinib (Xeljanz, Pfizer) ABT-494 (AbbVie), and filgotinib (GLPG0634, Galapagos and Gilead))(Sandborn, 2016).

VI. Modes of Administration

Any method known to those in the art for contacting a cell, organ, or tissue with compounds of the present technology may be employed. Suitable methods include in vitro, ex vivo, or in vivo methods.

In vitro methods typically include cultured samples. For example, a cell can be placed in a reservoir (e.g., tissue culture plate), and incubated with a compound under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are typically returned to the donor, placed in a recipient, or stored for future use. Thus, the compound is generally in a pharmaceutically acceptable carrier.

In vivo methods typically include the administration of a compound of the present technology to a mammal such as a human. When used in vivo for therapy, a compound of the present technology is administered to a mammal in an amount effective to obtain the desired result, e.g., of treating the mammal. The effective amount is determined during pre-clinical trials and clinical trials by methods familiar to physicians and clinicians. The dose and dosage regimen will depend upon the degree of the disease or condition in the subject, the characteristics of the particular compound of the present technology used, e.g., its therapeutic index, the subject, and the subject's history.

An effective amount of a compound of the present technology useful in the present methods, such as in a pharmaceutical composition or medicament, may be administered to a mammal in need thereof by any of a number of well-known methods for administering pharmaceutical compositions or medicaments. The compounds of the present technology may be administered systemically or locally.

The compounds of the present technology described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

In some embodiments, the pharmaceutical compositions of the present disclosure contain a pharmaceutically acceptable carrier and/or excipient suitable for rendering the compound or mixture administrable orally as a tablet, capsule or pill, or parenterally, intravenously, intradermally, intramuscularly or subcutaneously, or transdermally.

Pharmaceutical compositions are typically formulated to be compatible with the intended route of administration. Administering the pharmaceutical composition of the present disclosure may be accomplished by any means known to the skilled artisan. Routes of administration include, but are not limited to, parenteral, intravenous, intramuscular, intradermal, intraperitoneal, intratracheal, subcutaneous, oral, intranasal/respiratory (e.g., inhalation), transdermal (topical), sublingual, ocular, vaginal, rectal, and transmucosal administration. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection. e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In some embodiments, administration is topical and/or at the luminal surface of the tissue to be treated. "Topical" administration of a composition means contacting the composition with the skin. "Luminal surface" refers to the inner open space or cavity of a tubular organ, such as the interior central space in an artery or vein through which blood flows; the interior of the gastrointestinal tract; the pathways of the bronchi in the lungs; the interior of renal tubules and urinary collecting ducts; the pathways of the female genital tract, starting with a single pathway of the vagina, splitting up in two lumina in the uterus, both of which continue through the fallopian tubes.

In some embodiments, the compounds of the present technology are administered topically and/or at a luminal surface of the target tissue. This is advantageous to reduce potential systemic toxic side effects of the compounds.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

EXPERIMENTAL EXAMPLES

The present technology is further illustrated by the following examples, which should not be construed as limiting in any way.

Example 1: Synthesis of BT117

An illustrative example of the general synthesis of a PEG conjugate (BT117) is shown in Scheme 1.

Scheme 1
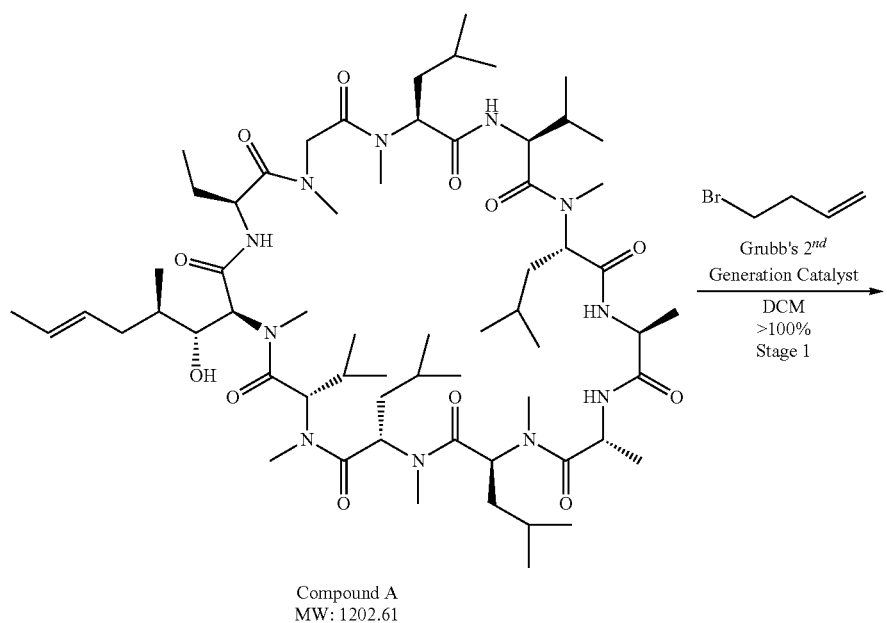
Compound A
MW: 1202.61
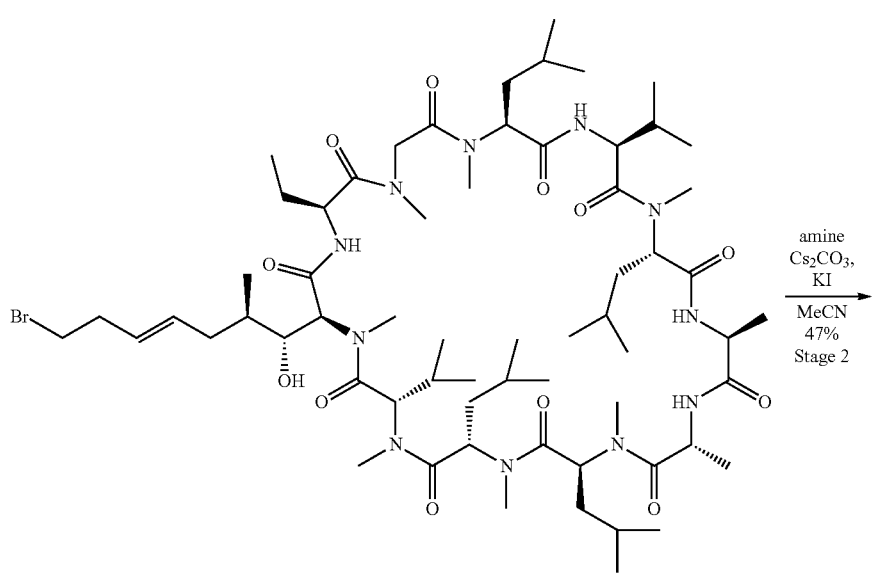
Compound H
MW: 1295.56

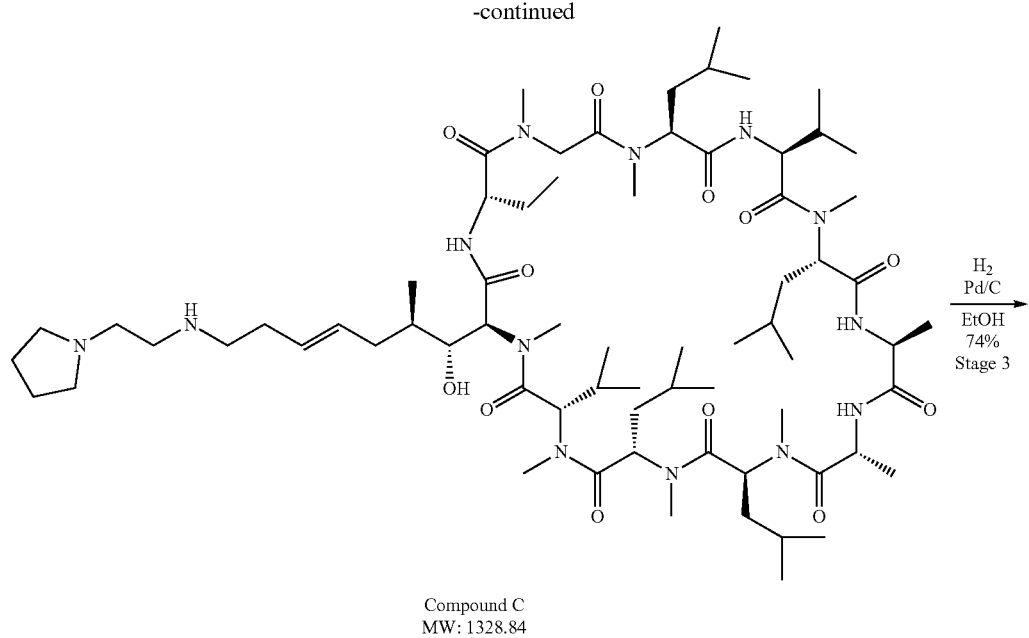
Compound C
MW: 1328.84
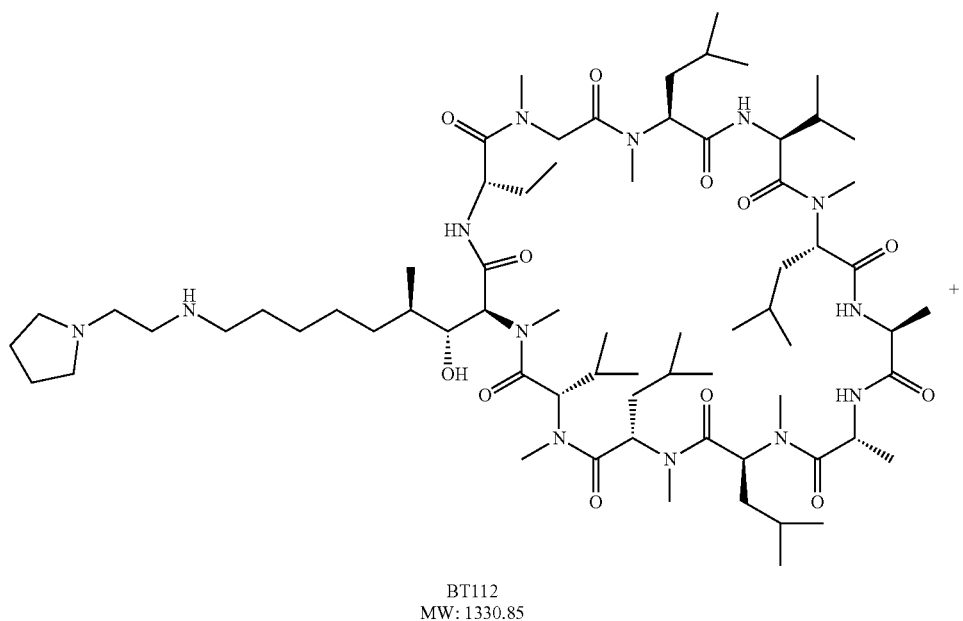
BT112
MW: 1330.85
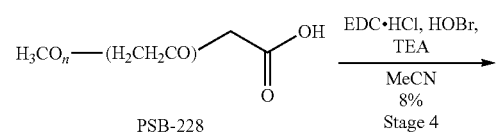
PSB-228
EDC·HCl, HOBr,
TEA
⟶
MeCN
8%
Stage 4

-continued

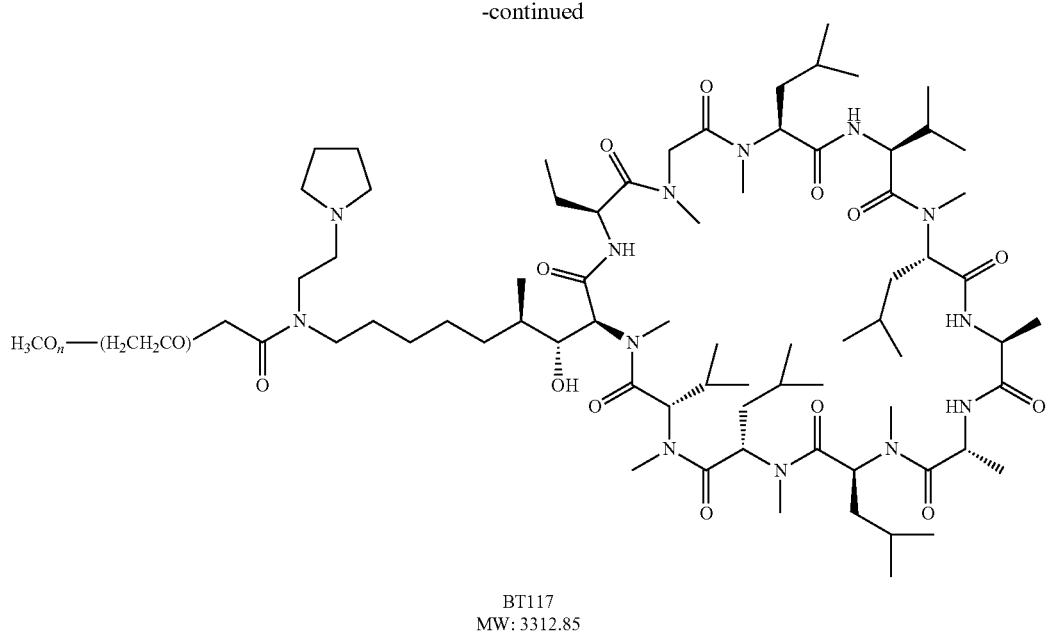

BT117
MW: 3312.85

Synthesis of Compound B. To a 1-L, round-bottom flask equipped with an overhead stirrer and a condenser purged with nitrogen was charged Cyclosporin A (20 g, 0.017 mole, 1 equiv, Shanghai lot #TL-CA180628), anhydrous dichloromethane (400 mL, 20 vol, Aldrich lot #SHBG6426V), and 4-bromobut-1-ene (25 mL, 0.249 mole, 15 equiv, Aldrich lot #BCBP4275V). The resulting solution was degassed for 11 min by purging with nitrogen. To the solution was added Grubb's 2nd generation catalyst (3.53 g, 0.004 mole, 0.25 equiv, Astatek lot #P164-00001) and the resulting suspension was degassed for 4 min by purging with nitrogen. The reaction mixture was heated at a gentle reflux at 40° C. with vigorous stirring under a blanket of nitrogen for 17 h. The reaction mixture was cooled to room temperature, concentrated to dryness under reduced pressure, and purified by Combiflash (0-10% methanol/dichloromethane) to give a brown product (25 g, 116%) as a mixture of Compound B and Cyclosporin A. LC-MS confirmed the product mass ([M+1]1297) and analysis by $^1$H NMR supported the formation of the structure (see FIG. 1).

Figure 2:
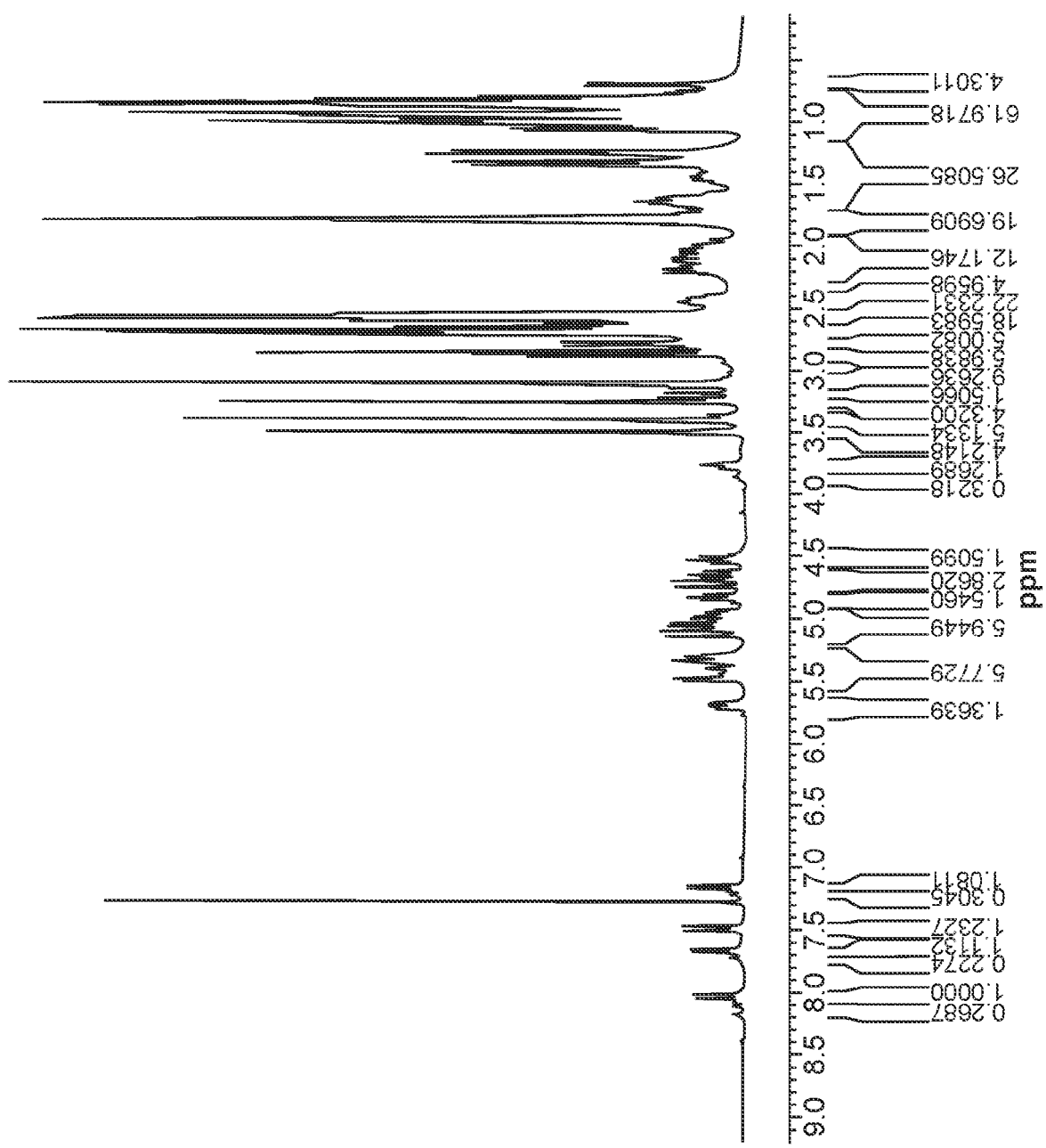
FIG. 2 is a $^1$H NMR (CDCl$_3$, 300 MHz) spectrum of compound C (Example 1).

Synthesis of Compound C. To a 1-L, round-bottom flask equipped with stirring bar was charged IBR-D-1 (22 g, 0.018 mole. 1 equiv), cesium carbonate (23.84 g, 0.0731 mole, 4 equiv, Aldrich lot #0000066667), potassium iodide (2.64 g, 0.016 mole, 0.87 equiv, Aldrich lot #BCBX6003), and acetonitrile (140 mL, 6.3 vol, Fischer lot #189015). The reactor was capped with a septa and purged with nitrogen for 15 min while stirring. 1-(2-Aminoethyl)pyrrolidine (9.27 mL, 0.073 mole, 4 equiv, Combi-blocks lot #7154-73-6) was charged to the reactor via syringe and the reaction mixture was stirred overnight at room temperature under nitrogen. Analysis of the reaction mixture by thin layer chromatography (TLC)(30% methanol/dichloromethane) showed a highly polar product on the baseline. The batch was diluted with dichloromethane (1 L, bulk) and transferred to a 2-L, separation funnel. The batch was washed with 0.5N NaOH (2×100 mL) followed by brine solution (200 mL). The aqueous layers were combined and back extracted with dichloromethane (bulk. 200 mL). The organic layers were combined, dried over anhydrous sodium sulfate, and evaporated to dryness under reduced pressure. The residue was purified by Combiflash gradient of (0-100% methanol/dichloromethane). The product eluted at 30-40% methanol/dichloromethane. TLC was visualized by KMNO$_4$ solution. The highly polar fractions close to the base line were collected and concentrated under reduced pressure. The residue was kept under high vacuum overnight to give a gray solid (6.5 g, 27%). LC-MS confirmed the product mass ([M+1] 1329, [M+Na] 1352) and analysis by $^1$H NMR supported the formation of the structure (see FIG. 2).

Figure 3:
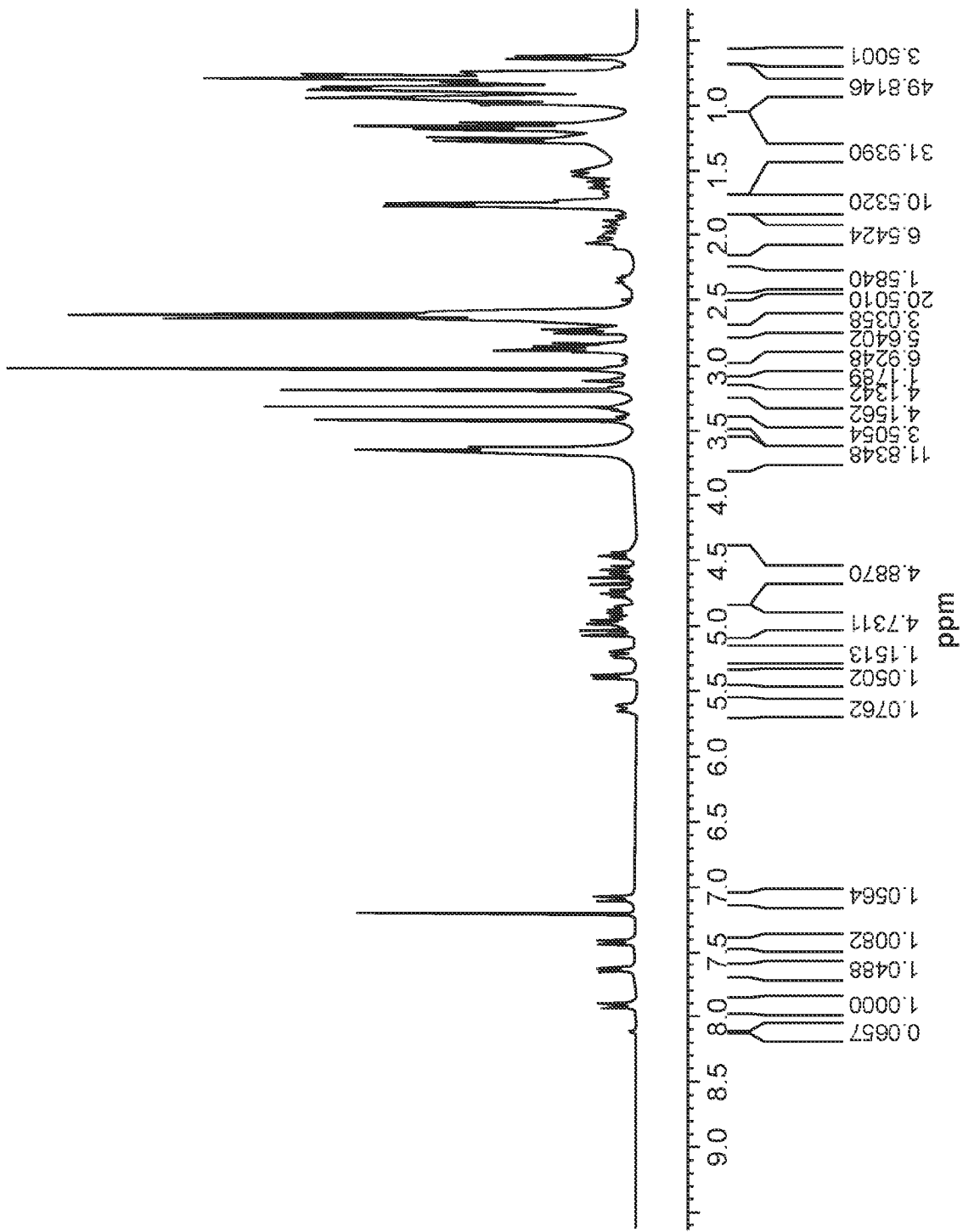
FIG. 3 is a $^1$H NMR (CDCl$_3$, 300 MHz) spectrum of BT112 (Example 1).

Synthesis of Intermediate BT112. To a three-neck, 1-L round-bottom flask equipped with stirring bar was charged Compound C (5.7 g, 0.0044 mole, lot #IBR-D-4), ethanol (324 mL, 60 vol, bulk), and 10% Pd/C (9.88 g, 180 wt %, Aldrich lot #MKCG8458). The reactor was capped with a septa and purged with nitrogen (3×) by evacuation and refilling. It was then purged with hydrogen (3×) by evacuation and refilling. The reaction mixture was held under positive hydrogen pressure overnight by means of two hydrogen balloons. The batch was filtered over Celite then thorough a 0.2-Micron PVDF filter syringe to afford a clear yellow solution. The solution was evaporated under reduced pressure to afford yellowish white solid (4.7 g, 81%). LC-MS confirmed the product mass ([M+1]1331) and analysis by $^1$H NMR supported the formation of the structure (see FIG. 3). No further purification was performed.

Figure 4:
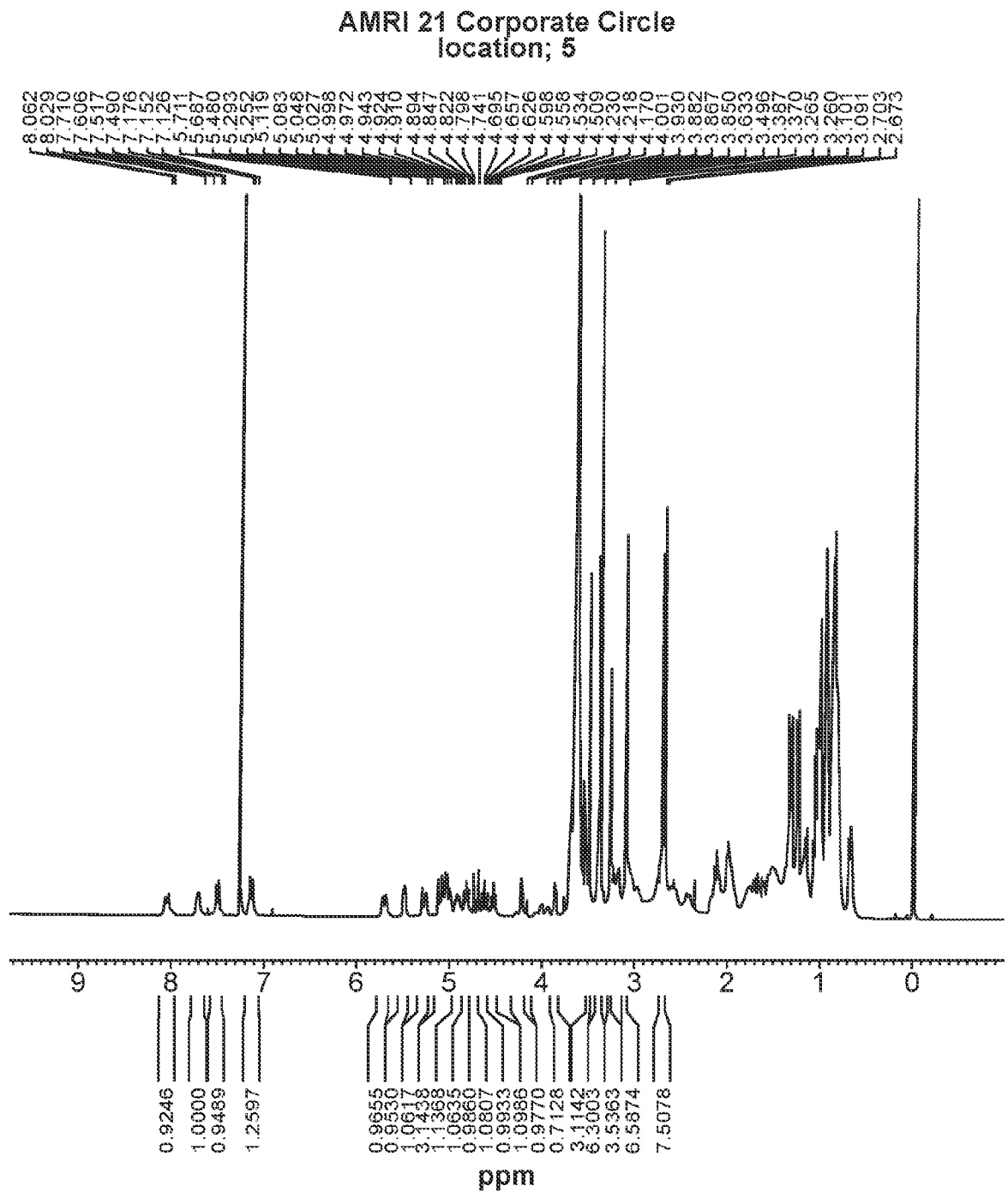
FIG. 4 is a $^1$H NMR (CDCl$_3$, 300 MHz) spectrum of BT117 (Example 1).

Synthesis of BT117. 1.0 eq. BT112 and 1.25 eq. PSB-228 (Creative PEGWorks) were combined with 1.4 eq. EDCI, 1.25 eq. HOBt, and S eq. TEA in acetonitrile (50 vol) at room temperature and stirred for 19 h. The crude product was purified by extraction and silica chromatography to give product (0.016 g) as a white solid. PBS-228 is a linear methoxy PEG carboxyl with a molecular weight of approximately 2000 Da (see FIG. 4).

Example 2: Inhibition of Neutrophil Migration by Compounds of the Present Technology This example demonstrates the efficacy of the compounds of the present technology in inhibiting neutrophil migration in vitro, and that the compounds of the present technology exhibit a dose-responsive inhibition of neutrophil migration.

PMN transmigration assay. T84 colorectal cancer cells were grown to confluence on the bottom side of 12 well polycarbonate membrane inserts of a 24 well Transwell® plate. The confluent growth of these epithelial cells results in physiologically-relevant apical (luminal) and basolateral surfaces in the transwells.

The apical surface of the monolayer was treated with BT117 over a dose range for 1 hour. The monolayer was then infected on the apical surface with *Salmonella* typhimurium for 2 hours to induce hepoxilin A3 ($HXA_3$) efflux through the MRP2 membrane protein and into the apical chamber.

The bacteria were washed off the monolayer and the apical surface re-exposed to BT117. Freshly isolated and prepared human neutrophils were then added to the basolateral side and allowed to transmigrate through the monolayer for 2 hours. The number of neutrophils migrated to the apical chamber (due to the $HXA_3$ gradient) was then assayed by determination of myeloperoxidase activity (a neutrophil biomarker). Inhibition of transmigration is indicated by lower MP) activity in the apical chamber.

Figure 5:
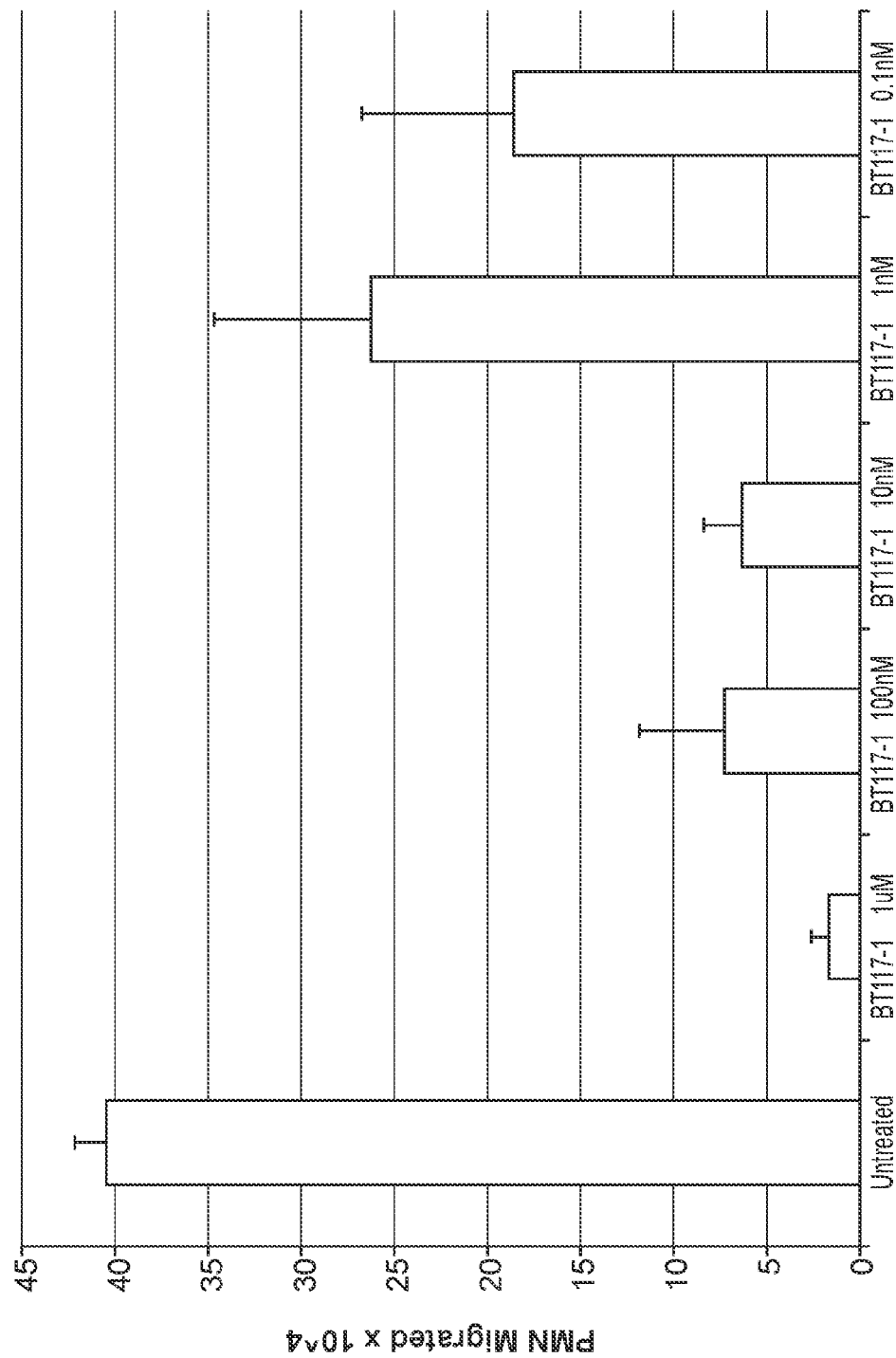
FIG. 5 is a chart showing the inhibition of neutrophil migration by BT117 as measured by the PMN transmigration assay.

Results. As shown in FIG. 5, BT117 inhibits neutrophil migration. A 50% inhibition was observed at compound concentrations between 1 nM and 10 nM. Accordingly, these results demonstrate that compounds of the current technology are useful in methods for inhibiting neutrophil migration, such as methods for the prevention or treatment of diseases or conditions caused by, resulting in, or otherwise associated with neutrophil migration.

Example 3: Compounds of the Present Technology for the Prevention and Treatment of Colitis This example demonstrates the use of compounds of the present technology for the prevention and treatment of colitis in animal models and human subjects.

Animal Models

Animal models suitable for use in this example include, but are not limited to, animals having colitis, such as those described herein. One of skill in the art will understand that the following description is illustrative and may be applied as appropriate to other animal models.

General. C57BL/6 and cnr2-/- mice will be purchased from Jackson laboratories; FVB wt and mdr1a-/- will be purchased from Taconic. Female mice are used at age 6-12 weeks, and genotypes are mixed for at 2-4 weeks prior to experiments to equalize the microbiota. Mice are treated with 3% DSS (molecular weight 36,000-50,000, MP Biomedicals) in the drinking water for 7 days, then placed back on normal water and sacrificed at day 9, which represented peak disease. Samples from mid and distal colon are fixed in 10% formalin, paraffin-embedded, sectioned, and stained for histopathological analysis with hematoxylin and eosin. Each sample is graded semi-quantitatively from 0 to 3 for four criteria: (1) degree of epithelial hyperplasia and goblet cell depletion; (2) leukocyte infiltration in the *Lamina propria*; (3) area of tissue affected; and (4) the presence of markers of severe inflammation such as crypt abscesses, submucosal inflammation, and ulcers. Samples are scored by a trained investigator blinded to sample identity, and mid and distal values are averaged to give colon histopathology score.

Subjects are administered compounds of the present technology according to methods described herein, such as by intrarectal administration. In some embodiments, the compound is administered once daily, once weekly, or once monthly. In some embodiments, compounds are administered multiple times daily, multiple times weekly, or multiple times monthly. Control subjects are administered vehicle alone.

Isolation of *Lamina propria* leukocytes and flow cytometry. Cell suspensions from the *Lamina propria* are prepared as described previously (Buonocore et al., 2010). Intestinal tissue is cut into small pieces, treated with RPMI with 10% FBS and 5 mM EDTA to remove epithelial cells, and then incubated with 100 U/mL Collagenase Type VIII (Sigma-Aldrich) for two 1 hr periods. Cells are then applied to a discontinuous 30/40/75% gradient of Percoll (GE Healthsciences) and harvested from the 40/70% interface. Cells are washed in PBS/0.1% BSA, incubated with anti-Fc receptor ($\alpha$CD16/32, eBioscience) and stained with Zombie Live/Dead infrared stain (eBioscience) then surface stained with antibodies to CD45, CD11b, Ly6G, and Ly6C or Gr1. Samples are run on a MACSquant Analyzer 10 (Miltenyi Bioscience) and analyzed using Flowjo software Version 10 (Treestar).

Analysis of myeloperoxidase content in mouse samples. Samples are assayed for myeloperoxidase activity as described. Tissue sections of colon are frozen in liquid $N_2$ and stored at −80° C. until use. Sections are put in hexadecyl trimethyl ammonium bromide (HTAB, Sigma) buffer with lysing matrix D (MP Biomedicals) and homogenized with a FastPrep-24 homogenizer at level 6 for 40 s. Samples are combined with ABTS and fluorescence read over 8 min. Slopes are calculated by linear regression using Graphpad Prism, and normalized to protein content for individual samples as measured by Bicinchonic Acid assay (BioRad). For analysis of fecal samples, fecal contents are weighed and HTAB buffer added at a ratio of 10 μL/mg, and calculated slopes are used directly.

Mass spectrometric analysis of $HXA_3$ in colonic mucosa. Mice are administered 5% DSS in their drinking water and sacrificed on day 7. The proximal colon from untreated or DSS-treated mice (9 mice/cohort) is harvested and three intestinal segments pooled. Mucosal scrapings are collected by scraping intestinal surfaces with a rubber policeman in PBS, and HXA content is analyzed as previously described (Mumy, K. L. et al., *Infect. Immun.* 76:3614-3627 (2008).

Results. It is expected that intrarectal administration of compounds of the present technology will significantly reduce intestinal pathology and colon shortening induced by DSS as compared to control animals. Analysis of colon histopathology will show that mice treated with the compounds have reduced neutrophil infiltration into the colonic lumen, which will be confirmed by a significant reduction in myeloperoxidase in fecal samples.

Accordingly, these results show that the compounds of the present technology are useful in methods of reducing neutrophil infiltration in vivo, such as in the prevention and treatment of inflammatory condition associated with neutrophil migration, such as colitis.

Human Subjects

Human subjects diagnosed as having or suspected to have colitis or a related disorder and presently displaying one or more symptoms and/or pathologies of colitis or a related disorder, are recruited using selection criteria known and accepted in the art.

Methods of Prevention and Treatment: Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered compounds of the present technology prior to or subsequent to the development of symptoms and/or pathologies of colitis or related disorders and assessed for reversal of symptoms/pathologies or attenuation of expected symptoms/pathologies using methods known in the art.

Results: it is expected that compounds of the present technology will induce reversal of symptoms and/or pathologies of colitis and related disorders in human subjects. These results will show that compounds of the present technology are useful and effective for the prevention and treatment of such disorders.

Example 4: Compounds of the Present Technology for the Prevention and Treatment of Neutrophil-Mediated Skin Disorders This example demonstrates the use of compounds of the present technology for the prevention and treatment of neutrophil-mediated skin disorders such as dermatitis (eczema), rosacea, seborrheic dermatitis, and psoriasis in animal models and human subjects. One of skill in the art will understand that the example set forth below relating to psoriasis is illustrative of neutrophil-mediated skin disorders, with methods generally applicable to any neutrophil-mediated skin disorder.

Animal Models

Animal models suitable for this example include any accepted psoriasis model, including, but not limited to, models having spontaneous mutations, genetically engineered animals, immunological models, and pharmacological models. Spontaneous mutation models include but are not limited to mice homozygous for the asebia ($Scd1^{ab}/Scd1^{ab}$), chronic proliferative dermatitis ($Sharpin^{cpdm}/Sharpin^{cpdm}$), flaky skin ($Ttc7^{fsn}/Ttc7^{fsn}$) mutations. Genetically engineered models include animals ectopically expressing key regulatory molecules or lacking key regulatory molecules as known in the art. Immunological models include animal subjects subjected to adoptive transfer or related methods as known in the art. Pharmacological models include subjects administered agents that induce psoriasis or psoriasis-related conditions. For example, subjects topically administered imiquimod (IMQ), a toll-like receptor (TLR)-7 and TLR-8 agonist.

One of skill in the art will understand that the following description is illustrative and may be applied as appropriate to other animal models.

Materials. Imiquimod (IMQ, 5% cream, Beselna®) is purchased from Mochida Pharmaceutical (Tokyo, Japan). Betamethasone butyrate propionate (0.05% ointment, Antebate®) is purchased from Torii Pharmaceutical (Tokyo, Japan). Real-time PCR probes and related agents is purchased from Applied Biosystems (Massachusetts, USA).

Animals. Female BALB/c mice and male CB-17 scid mice aged 7-12 weeks old are housed under specific pathogen-free conditions at a room temperature of 23±3° C. and air humidity of 55±15% in a 12-hour light/dark cycle environment, and provided with food and water ad libitum.

Induction of skin inflammation. IMQ 5% cream is applied on inner and/or outer sides of the left ear skin once daily. The dose of IMQ is either 250 ug on outer side, 500 ug on outer side, or 250 ug on both inner and outer sides of the ear. Betamethasone ointment or relevant ointment base is applied twice daily on to the left ear, at a volume of 5 uL to both the inner and/or outer sides. Thickness of the left ear is measured as a quantitative index of skin inflammation utilizing a thickness gauge (IDA-112M, Mitutoyo, Kawasaki, Japan) once daily before the application of IMQ. Control subjects are administered vehicle alone.

For methods of prevention, subjects are pre-treated with compounds of the present technology by topical application for a pre-determined period prior to IMQ exposure.

For methods of treatment, subjects are topically administered compounds of the present technology for a pre-determined period following confirmation of IMQ-induced inflammation using methods known in the art.

Subjects are euthanized by carbon dioxide gas, and the left ear harvested after examination of gross morphology for erythema and scaling. A portion of the harvested tissue is sliced, fixed with buffered 10% formalin solution, and processed for preparation of histological paraffin sections. The sections are stained with hematoxylin and eosin, and subjected to light microscopic examination. The remaining tissue is stored at −80° C. for mRNA analysis by real time PCR.

Real time PCR assays. Total RNA samples in the ear tissues are obtained with RNeasy® Lipid Tissue Mini Kit (QIAGEN, Venlo, the Netherlands), following the manufacturer's instructions. The level of transcripts coding cytokines of interest in the present study are measured by the TaqMan Gene Expression Assays using the RNA-to-Ct™ 1-Step Kit.

Illustrative targets include but are not limited to IFN-γ, IL-13, IL-17, IL-22, IL-23, TNF-α, and IL-1β. Target transcript levels are normalized to GAPDH transcript levels.

Statistical Analysis. Values of ear thickness are shown as increases from the pre-treatment values measured at Day 1 and expressed as mean±standard deviation (S.D.). Statistical significance is analyzed by F-test followed by Aspin-Welch's t-test and Bartlett's test followed by Dunnett's test or Steel test in ear thicknesses, and by Bartlett's test followed by Tukey's test or Steel-Dwass test in mRNA transcript levels. A p value of less than 0.05 was considered statistically significant.

Results. It is predicted that administration of compounds of the present technology will prevent or reduce IMQ-induced inflammation as measured by tissue thickness, inflammatory gene expression, and dermal neutrophil infiltration. These results will show that compounds of the present technology are useful in the prevention and treatment of conditions associated with inflammation and dermal neutrophil infiltration, including but not limited to dermatitis (eczema), rosacea, seborrheic dermatitis, and psoriasis.

Human Subjects

Human subjects diagnosed as having or suspected to have a neutrophil-mediated skin disorder, such as dermatitis (eczema), rosacea, seborrheic dermatitis, or psoriasis, and presently displaying one or more symptoms and/or pathologies of the disorder, are recruited using selection criteria known and accepted in the art.

Methods of Prevention and Treatment. Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered compounds of the present technology prior to or subsequent to the development of symptoms and/or pathologies of neutrophil-mediated skin disorder and assessed for reversal of symptoms/pathologies or attenuation of expected symptoms/pathologies using methods known in the an. For example, subjects are administered compounds of the present technology prior to or subsequent to the development of a neutrophil-mediated skin disorder or symptoms thereof. Subjects are then assessed for prevention, reversal, or attenuation of the disorder or symptom using methods known in the art.

Results. It is expected that compounds of the present technology will induce reversal of symptoms and/or pathologies of neutrophil-mediated skin disorders, such as dermatitis (eczema), rosacea, seborrheic dermatitis, and psoriasis. These results will show that compounds of the present technology are useful and effective for the prevention and treatment of neutrophil-mediated skin disorders in human subjects.

Example 5: Compounds of the Present Technology for the Prevention and Treatment of Celiac Disease This example demonstrates the use of compounds of the present technology for the prevention and treatment of celiac disease. One of skill in the art will understand that the example set forth below is illustrative of gluten intolerance disorders generally, with methods generally applicable to celiac disease and related disorders.

Animal Models

Animal models suitable for this example include any accepted celiac model, including, but not limited to, spontaneous models such as dog and monkey models known in the art, induced models such as germ-free Wistar AVN rats administered gliadin immediately after birth, and transgenic models such as animals overexpressing IL-15. One of skill in the art will understand that the following description is illustrative and may be applied as appropriate to other animal models.

General. Animal models are selected and maintained according to relevant standards known in the art. Subjects are administered compounds of the present technology according to methods described herein, such as by oral administration. In some embodiments, the compound is administered once daily, once weekly, or once monthly. In some embodiments, compounds are administered multiple times daily, multiple times weekly, or multiple times monthly. Control subjects are administered vehicle alone.

For methods of prevention, subjects are administered compounds of the present technology prior to or subsequent to the development of symptoms and/or pathologies of celiac disease or related disorders and assessed for reversal of symptoms/pathologies or attenuation of expected symptoms/pathologies using methods known in the art.

Results: It is expected that compounds of the present technology will induce reversal of symptoms and/or pathologies of celiac disease and related disorders in animal models. These results will show that compounds of the present technology are useful and effective for the prevention and treatment of celiac disease and related disorders.

Human Subjects

Human subjects diagnosed as having or suspected to have celiac disease or a related disorder and presently displaying one or more symptoms and/or pathologies of celiac disease or a related disorder, are recruited using selection criteria known and accepted in the art.

Methods of Prevention and Treatment: Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

For methods of prevention, subjects are administered compounds of the present technology prior to or subsequent to the development of symptoms and/or pathologies of celiac disease or related disorders and assessed for reversal of symptoms/pathologies or attenuation of expected symptoms/pathologies using methods known in the an.

Results: It is expected that compounds of the present technology will induce reversal of symptoms and/or pathologies of celiac disease and related disorders in human subjects. These results will show that compounds of the present technology are useful and effective for the prevention and treatment of celiac disease and related disorders.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

Each and every publication and patent mentioned in the above specification is herein incorporated by reference in its entirety for all purposes. Various modifications and variations of the described methods and system of the present technology will be apparent to those skilled in the art without departing from the scope and spirit of the present technology. Although the present technology has been described in connection with specific embodiments, the present technology as claimed should not be unduly limited to such specific embodiments. Indeed, various modifications of the described modes for carrying out the present technology which are obvious to those skilled in the art and in fields related thereto are intended to be within the scope of the following claims.

What is claimed is:

1. A compound having the structure of Formula I,

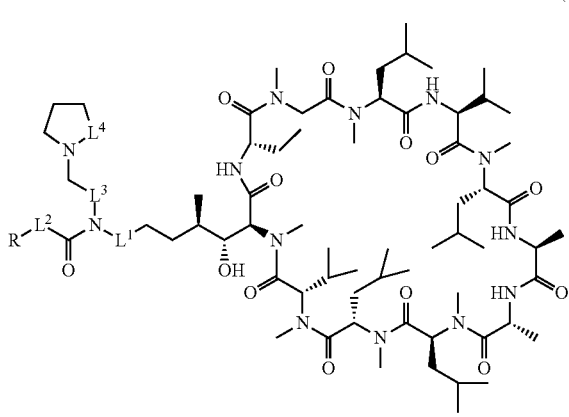

(I)

a stereoisomer thereof, or a pharmaceutically acceptable salt of the foregoing, wherein
$L^1$ is a $C_{1-6}$ alkylene group optionally substituted with one or more F;
$L^2$ is absent or is a linker selected from O, NH, or a $C_{1-12}$ alkylene or heteroalkylene group;
$L^3$ is a $C_{1-6}$ alkylene group;
$L^4$ is a methylene or ethylene group; and
R is a polyethylene glycol (PEG) group.

2. The compound of claim 1 wherein $L^1$ a $C_{1-6}$ alkylene group.

3. The compound of claim 1 wherein $L^1$ is a propylene group.

4. The compound of claim 1 wherein $L^2$ is absent.

5. The compound of claim 1 wherein $L^2$ is a $C_{1-6}$ alkylene group.

6. The compound of claim 1 wherein $L^2$ is a methylene group.

7. The compound of claim 1 wherein $L^3$ is a methylene group.

8. The compound of claim 1 wherein $L^4$ is a methylene group.

9. The compound of claim 1 wherein R is a PEG terminated with OH or a $C_{1-6}$ alkoxy group.

10. The compound of claim 1 wherein R is a PEG having a weight average molecular weight of from about 100 Da to about 0.5 kDa.

11. The compound of claim 1 wherein R is a PEG having a weight average molecular weight of from about 1 kDa to about 5 kDa.

12. The compound of claim 1 wherein R is a PEG having a weight average molecular weight of about 2 kDa.

13. The compound of claim 1 having the structure of Formula IA or a pharmaceutically acceptable salt thereof:

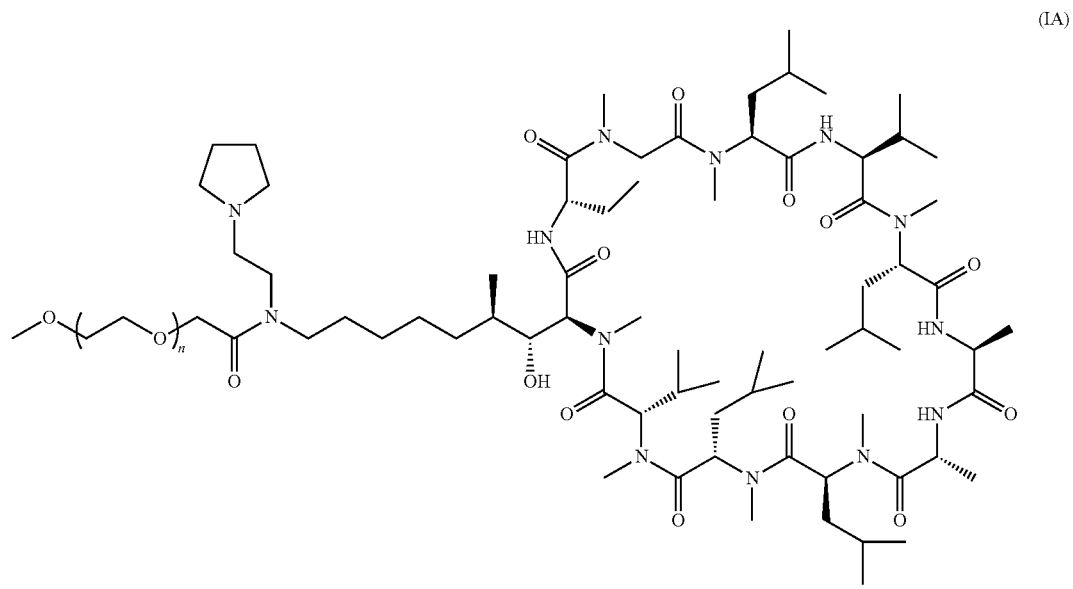

(IA)

wherein n is an integer from 40 to 50.

14. A pharmaceutical composition comprising the compound of claim 1 and a pharmaceutically acceptable carrier.

15. A method for treating a disease associated with neutrophil-mediated inflammation in a target tissue of a mammalian subject in need thereof, comprising administering to the subject a therapeutically effective amount of a compound of formula I:

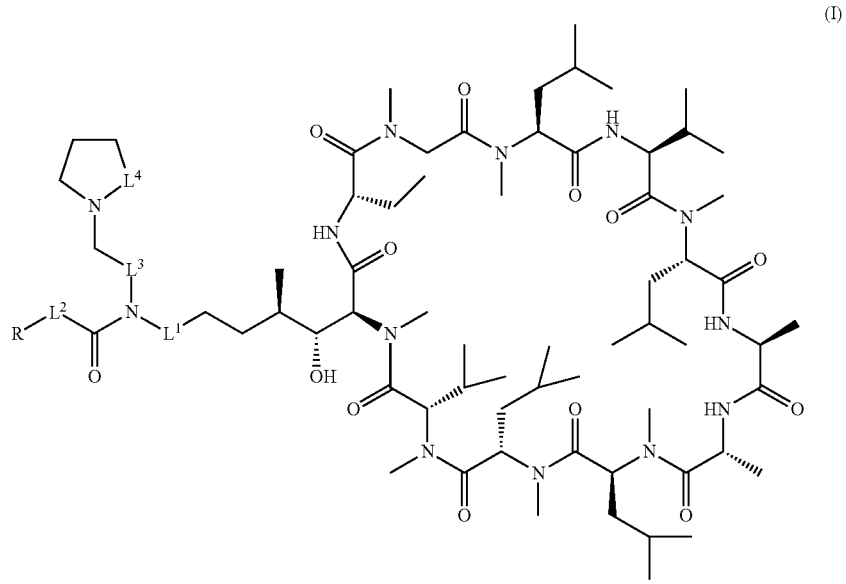

(I)

a stereoisomer thereof, or a pharmaceutically acceptable salt of the foregoing, wherein

- $L^1$ is a $C_{1-6}$ alkylene group optionally substituted with one or more F;
- $L^2$ is absent or is a linker selected from O, NH, or a $C_{1-12}$ alkylene or heteroalkylene group;
- $L^3$ is a $C_{1-6}$ alkylene group;
- $L^4$ is a methylene or ethylene group; and
- R is a polyethylene glycol (PEG) group, wherein the disease is:

an intestinal disease selected from the group consisting of Crohn's disease, celiac disease, ulcerative colitis, infectious/non-infectious enterocolitis, and inflammatory bowel disease (IBD);

an inflammatory skin disease selected from the group consisting of dermatitis, rosacea, seborrheic dermatitis, and psoriasis; or an ocular disease selected from the group consisting of uveitis, retinitis, keratitis, and macular degeneration.

16. The method of claim 15, wherein the compound has the structure of Formula IA or a pharmaceutically acceptable salt thereof:

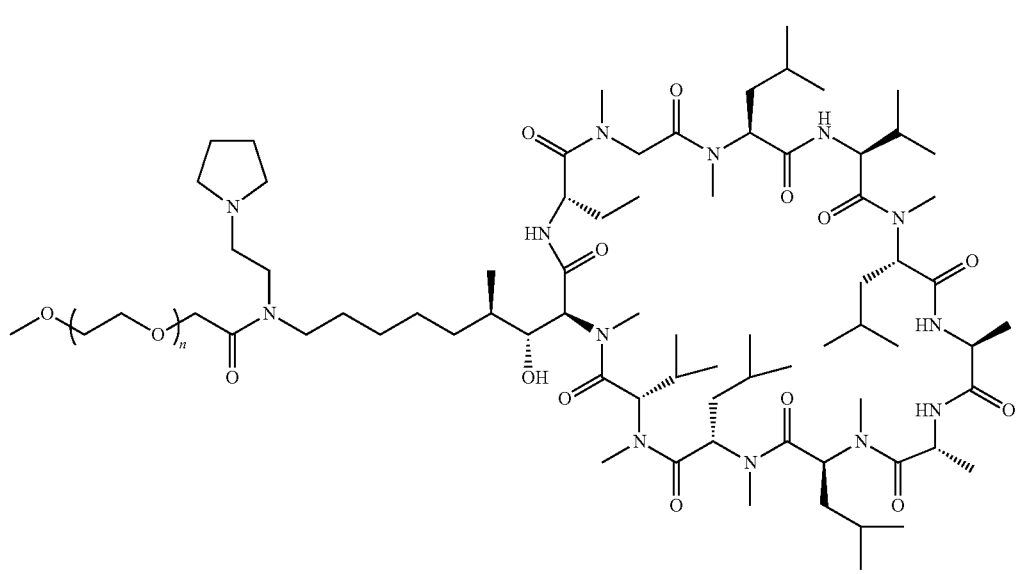

(IA)

wherein n1 is an integer from 40 to 50.

17. The method of claim 15, wherein the method further comprises:

administering to the subject a therapeutically effective amount of one or more antibiotic and/or anti-inflammatory agent selected from the group consisting of: Dalbavancin, Oritavancin, Daptomycin, Tedizolid, Ceftobiprole, Ceftolozane-tazobactam, mupirocin, neomycin sulfate bacitracin, polymyxin B, 1-ofloxacin, clindamycin phosphate, gentamicin sulfate, metronidazole, hexylresorcinol, methylbenzethonium chloride, phenol, a quaternary ammonium compound, tea tree oil, a steroidal agent selected from the group consisting of hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone diflorasone diacetate, diflucortolone valerate, flurandrenolone, fluclorolone acetonide, fludrocortisone, flumethasone pivalate, fluosinolone acetonide, fluocinonidea, fluocortin butylester, fluocortolone, fluprednidene acetate, flurandrenolone, halcinonide, hydrocortisone acetate, hydrocortisone butyrate, methylprednisolone, triamcinolone acetonide, cortisone, cortodoxone, flucetonide, fludrocortisone, diflorasone diacetate, flurandrenolone acetonide, medrysone, amciafel, amcinafide, betamethasone, chloroprednisone, chloroprednisone acetate, clocortolone, clescinolone, dichlorisone, difluprednate, flucloronide, flunisolide, fluoromethalone, flupredniso-lone, hydrocortisone valerate, hydrocortisone cyclopentyl proprionate, hydrocortamate, meprednisone, paramethasone, prednisolone, prednisone, beclomethasone dipropionate, betamethasone dipropionate, and triamcinolone, a COX inhibitor, a LOX inhibitor, a p38 kinase inhibitor, cyclosporin, tetracycline, minocycline, and doxycycline, or any combination thereof; and/or administering to the subject a therapeutically effective amount of one or more antibodies targeting *Clostridium difficile* toxins, antibodies targeting tumor necrosis factor (TNF), antibodies targeting interleukins, and antibodies targeting metalloproteinase-9.

18. The compound of claim 1, wherein $L^1$ is a $C_{1-6}$ alkylene group;

$L^2$ is absent or is a $C_{1-6}$ alkylene group;

$L^3$ is a methylene group;

$L^4$ is a methylene group; and

R is a PEG having a weight average molecular weight of from about 1 kDa to about 5 kDa.

* * * * *

UNITED STATES PATENT AND TRADEMARK OFFICE
CERTIFICATE OF CORRECTION

PATENT NO. : 12,421,281 B2  
APPLICATION NO. : 17/891351  
DATED : September 23, 2025  
INVENTOR(S) : Chris Murphy, Ronald Farquhar and Roland E. Dolle Page 1 of 1

It is certified that error appears in the above-identified patent and that said Letters Patent is hereby corrected as shown below:

In the Claims

Column 46, Claim 16, Line 60 "wherein n1 is an integer from 40 to 50." should read -- wherein n is an integer from 40 to 50. --

Column 46, Claim 17, Line 65 "agent" should read -- agents --.

Column 47, Claim 17, Line 13 "fluocinonidea" should read -- fluocinonide --.

Column 47, Claim 17, Line 22 to Column 48, Claim 17, Line 1 "fluoromethalone, fluprednisolone" should read -- fluoromethalone, fluperolone, fluprednisolone --.

Signed and Sealed this  
Twenty-third Day of December, 2025

John A. Squires  
*Director of the United States Patent and Trademark Office*